(12) United States Patent
An et al.

(10) Patent No.: US 10,060,926 B2
(45) Date of Patent: Aug. 28, 2018

(54) METHOD FOR DIAGNOSING AND TREATING OVARIAN CANCER

(71) Applicant: SUNGKWANG MEDICAL FOUNDATION, Seoul (KR)

(72) Inventors: Hee Jung An, Seoul (KR); Ah Young Kwon, Seongnam-si (KR)

(73) Assignee: SUNGKWANG MEDICAL FOUNDATION, Seoul (KR)

( * ) Notice: Subject to any disclaimer, the term of this patent is extended or adjusted under 35 U.S.C. 154(b) by 0 days.

(21) Appl. No.: 15/817,581

(22) Filed: Nov. 20, 2017

(65) Prior Publication Data

US 2018/0095087 A1    Apr. 5, 2018

Related U.S. Application Data

(62) Division of application No. 15/363,456, filed on Nov. 29, 2016, now Pat. No. 9,915,661.

(30) Foreign Application Priority Data

Nov. 30, 2015    (KR) .................... 10-2015-0169286

(51) Int. Cl.
| | |
|---|---|
| *C07H 21/02* | (2006.01) |
| *C07H 21/04* | (2006.01) |
| *G01N 33/574* | (2006.01) |
| *C12Q 1/6886* | (2018.01) |
| *C12N 15/113* | (2010.01) |

(52) U.S. Cl.
CPC ..... *G01N 33/57449* (2013.01); *C12N 15/113* (2013.01); *C12Q 1/6886* (2013.01); *C12N 2310/14* (2013.01); *C12N 2320/30* (2013.01); *C12Q 2600/118* (2013.01); *C12Q 2600/136* (2013.01); *C12Q 2600/158* (2013.01); *G01N 2333/4703* (2013.01)

(58) Field of Classification Search
CPC .... C12N 15/111; C12N 15/113; A61K 31/713
See application file for complete search history.

(56) References Cited

U.S. PATENT DOCUMENTS

2010/0216137 A1    8/2010    Bankaitis-Davis

FOREIGN PATENT DOCUMENTS

WO    2016/066604    5/2016

OTHER PUBLICATIONS

Kwon et al.—"VAV3 Overexpressed in Cancer Stem Cells Is a Poor Prognostic Indicator in Ovarian Cancer Patients", Stem Cells and Development, vol. 25, No. 13, 2015, pp. 1521-1535.
Office Action dated Mar. 27, 2017 in Korean Patent Application No. 10-2015-0169286.
Kyong-Won Kang, et al., "Overexpression of goosecoid homeobox is associated with chemoresistance and poor prognosis in ovarian carcinoma" Oncology Reports, vol. 32, 2014, pp. 189-198.

*Primary Examiner* — Amy H Bowman
(74) *Attorney, Agent, or Firm* — Oblon, McClelland, Maier & Neustadt, L.L.P.

(57) ABSTRACT

Provided are a composition, a kit, and a method of predicting prognosis of ovarian cancer or a risk of recurrence of ovarian cancer. Provided are a composition for treating ovarian cancer or preventing recurrence of ovarian cancer and a method of screening a material for treating ovarian cancer or preventing recurrence of ovarian cancer. According to the present disclosure, prognosis or recurrence of ovarian cancer can be efficiently diagnosed, and a candidate material that can treat ovarian cancer or prevent recurrence of ovarian cancer can be efficiently screened.

4 Claims, 15 Drawing Sheets
Specification includes a Sequence Listing.

SPHEROID FORMATION ASSAY

SEQUENCE LISTING

<160> NUMBER OF SEQ ID NOS: 2

<210> SEQ ID NO 1
<211> LENGTH: 25
<212> TYPE: RNA

```
<213> ORGANISM: Artificial Sequence
<220> FEATURE:
<223> OTHER INFORMATION: VAV3 siRNA

<400> SEQUENCE: 1
caggaccaaa gagucaggag aauau                                     25

<210> SEQ ID NO 2
<211> LENGTH: 25
<212> TYPE: RNA
<213> ORGANISM: Artificial Sequence
<220> FEATURE:
<223> OTHER INFORMATION: VAV3 siRNA

<400> SEQUENCE: 2
auauucuccu gacucuuugg uccug                                     25
```

METHOD FOR DIAGNOSING AND TREATING OVARIAN CANCER

CROSS-REFERENCE TO RELATED APPLICATION

This application is a divisional application of U.S. application Ser. No. 15/363,456 filed Nov. 29, 2016, pending, and claims the benefit of Korean Patent Application No. 10-2015-0169286, filed on Nov. 30, 2015, in the Korean Intellectual Property Office, the disclosure of which is incorporated herein in its entirety by reference.

BACKGROUND

1. Field

One or more embodiments relate to compositions, kits, and methods for predicting prognosis of ovarian cancer or a risk of recurrence of ovarian cancer, and more particularly, to compositions for treating ovarian cancer or preventing recurrence of ovarian cancer and methods of screening a material for treating ovarian cancer or preventing recurrence of ovarian cancer.

2. Description of the Related Art

Ovarian carcinoma is a cancer that has the highest lethality among female malignancies, and this high lethality results from chemoresistance and frequent recurrence of ovarian carcinoma. Several agents have been developed to prevent or treat ovarian carcinoma, but the mortality and rate of recurrence of ovarian carcinoma are still high.

Recently, interest in cancer stem cells (CSCs), which exist in small numbers within tumors and have high tumorigenic capacity, has been increasing. CSCs were initially isolated from ovarian serous carcinomas (OSCs) by a spheroid formation assay, and are presumed to be one of the major causes of recurrence and chemoresistance of cancers. However, no effective strategies for reducing CSCs and lowering the high recurrence and mortality rates of ovarian cancer have been developed yet.

SUMMARY

One or more embodiments include a composition for diagnosing prognosis of ovarian cancer or a risk of recurrence of ovarian cancer of an individual.

One or more embodiments include a kit for diagnosing prognosis of ovarian cancer or a risk of recurrence of ovarian cancer of an individual.

One or more embodiments include a method of diagnosing prognosis of ovarian cancer or a risk of recurrence of ovarian cancer of an individual.

One or more embodiments include a composition for treating ovarian cancer or preventing recurrence of ovarian cancer.

One or more embodiments include a method of screening a material for treating ovarian cancer or preventing recurrence of ovarian cancer.

BRIEF DESCRIPTION OF THE DRAWINGS

These and/or other aspects will become apparent and more readily appreciated from the following description of the embodiments, taken in conjunction with the accompanying drawings in which:

FIG. 1A shows (a) low view, (b) high view, and (c) power view phase-contrast images of primary cultures of OSC cells with spheroid morphology; FIG. 1B is a graph showing consistent spheroid-forming capacity of the primary cancer cells between the first and second generations (2.17%-2.37%), indicating that the spheroid-forming cells (SFCs) exhibit self-renewing characteristics; and FIG. 1C is a graph showing significant expression of stem cell markers detected in SFCs (*P<0.05) (known markers of stem cells are used, and all markers, except CD117, are significantly overexpressed in SFCs, indicating that the SFCs are enriched in CSCs as compared with the cultured primary cells);

FIG. 2A shows results representing hierarchical clustering of significantly altered genes with at least 15-fold differences between SFCs and primary cancer cells, wherein the clustered expression data are displayed on a heat map with individual genes listed on the X-axis and Y-axis, the gray-scale depicts relative levels of gene expression in SFC samples compared with their corresponding primary cancer cells from light (for downregulation) to dark (for upregulation), and 28 genes were highly expressed in all four SFC samples as compared with control cells while 34 genes were downregulated in all four SFC samples as compared with control cells; FIG. 2B is a pie chart showing ontology of genes upregulated more than 2-fold in SFCs (P<0.05), wherein genes associated with apoptosis and proliferation account for 13%, genes associated with cell cycle account for 10%, genes associated with signal transduction and CSCs account for 8%, and genes associated with drug response account for 5%; and FIG. 2C is a graph showing validation by quantitative reverse transcription polymerase chain reaction (qRT-PCR) of genes that are significantly upregulated by cDNA microarray, wherein the qRT-PCR is performed on 17 sets of SFCs and parental cancer cells, and GSC (4.26-fold), VAV3 (7.05-fold), FOXA2 (12.06-fold), LEF1 (17.26-fold), COMP (21.33-fold), GRIN2A (9.36-fold), CD86 (23.14-fold), PYY (4.18-fold), NKX3-2 (10.35-fold), and PDK4 (74.26-fold) are significantly upregulated in SFCs as compared with parental cancer cells thereof (*P<0.05);

FIG. 5A shows results of a spheroid formation assay, wherein the number of spheroid formations decreases by 30% after treatment of VAV3 siRNA as compared with that of spheroid formations in a negative siRNA control, the size of spheroids is significantly decreased in VAV3 siRNA-treated SKpac cells as compared with that of spheroids in the negative siRNA control, and the graph represents the mean±standard error (*$P<0.001$); FIG. 5B shows results of a colony formation assay, wherein VAV3 knockdown cells are seeded at 300 cells per well and cultured for 14 days, and consequently, the number of colonies of VAV3 siRNA-treated SKpac cells decreases by 41% as compared with control cells treated with negative siRNA, and the graph represents the mean±standard error of triplicate experiments (*$P<0.001$); and FIG. 5C shows results of an MTT assay, wherein cell viability is assessed after VAV3 siRNA treatment, and consequently, cell viability decreases by 25% and 18% (*$P<0.05$) at 24 hours and 48 hours, respectively, in VAV3 siRNA-treated SKpac cells as compared with control cells treated with negative siRNA, and upon treatment with VAV3 siRNA and 40 nM PTX, the number of SKpac cells decreases by 27% and 16% (*$P<0.05$) at 24 hours and 48 hours, respectively, compared with that of control cells treated with PTX+negative siRNA, and the graph represents the mean±standard error of triplicate experiments.

DETAILED DESCRIPTION

Figure 1A:
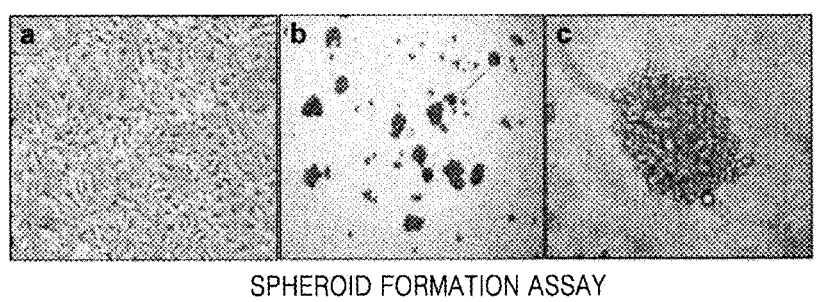
FIGS. 1A to 1C relate to cancer stem cells (CSCs) isolated from cultured primary cells from 17 ovarian serous carcinomas (OSCs) by a spheroid formation assay.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

According to one or more embodiments, there is provided a composition for predicting prognosis of ovarian cancer or a risk of recurrence of ovarian cancer of an individual, the composition including an agent for measuring an expression level of one or more genes selected from the group consisting of GSC, VAV3, FOXA2, LEF1, COMP, AZU1, GRIN2A, IL17F, CD86, PYY, FIGF, NKX3-2, WNT3A, and PDK4.

Goosecoid homeobox gene (GSC) may be a gene having an mRNA sequence of NCBI Accession No: NM_173849.2. Vav 3 guanine nucleotide exchange factor gene (VAV3) may be a gene having an mRNA sequence of NCBI Accession No: NM_006113.4 or NM_001079874.1. Forkhead box A2 gene (FOXA2) may be a gene having an mRNA sequence of NCBI Accession No: NM_021784.4 or NM_153675.2. Lymphoid enhancer-binding factor 1 gene (LEF1) may be a gene having an mRNA sequence of NCBI Accession No: NM_016269.4, NM_001166119.1, NM_001130714.2, or NM_001130713.2. Cartilage oligomeric matrix protein gene (COMP) may be a gene having an mRNA sequence of NCBI Accession No: NM_000095.2. Azurocidin 1 gene (AZU1) may be a gene having an mRNA sequence of NCBI Accession No: NM_001700.4. Glutamate receptor, ionotropic, N-methyl D-aspartate 2A gene (GRIN2A) may be a gene having an mRNA sequence of NCBI Accession No: NM_001134408.2, NM_000833.4, or NM_001134407.2. Interleukin 17F gene (IL17F) may be a gene having an mRNA sequence of NCBI Accession No: NM_052872.3. CD86 molecule gene (CD86) may be a gene having an mRNA sequence of NCBI Accession No: NM_001206925.1, NM_001206924.1, NM_176892.1, NM_175862.4, or NM_006889.4. Peptide YY gene (PYY) may be a gene having an mRNA sequence of NCBI Accession No: NM_004160.4. C-fos induced growth factor (vascular endothelial growth factor D) gene (FIGF) may be a gene having an mRNA sequence of NCBI Accession No: NM_004469.4. NK3 homeobox 2 gene (NKX3-2) may be a gene having an mRNA sequence of NCBI Accession No: NM_001189.3. Wingless-type MMTV integration site family member 3A gene (WNT3A) may be a gene having an mRNA sequence of NCBI Accession No: NM_033131.3. Pyruvate dehydrogenase kinase, isozyme 4 gene (PDK4) may be a gene having an mRNA sequence of NCBI Accession No: NM_002612.3.

The inventors of the present inventive concept have found that increased or decreased expression of GSC, VAV3, FOXA2, LEF1, COMP, AZU1, GRIN2A, IL17F, CD86, PYY, FIGF, NKX3-2, WNT3A, or PDK4 is associated with prognosis of ovarian cancer or recurrence of ovarian cancer. In this regard, an expression level of GSC, VAV3, FOXA2, LEF1, COMP, AZU1, GRIN2A, IL17F, CD86, PYY, FIGF, NKX3-2, WNT3A, or PDK4 may be considered when diagnosing prognosis of ovarian cancer or a risk of recurrence of ovarian cancer.

GSC, VAV3, FOXA2, LEF1, COMP, AZU1, GRIN2A, IL17F, CD86, PYY, FIGF, NKX3-2, WNT3A, and PDK4, which are proteins used in the present specification, are construed as including respectively naturally occurring wild-type GSC, VAV3, FOXA2, LEF1, COMP, AZU1, GRIN2A, IL17F, CD86, PYY, FIGF, NKX3-2, WNT3A, and PDK4, or functional variants thereof. In addition, GSC, VAV3, FOXA2, LEF1, COMP, AZU1, GRIN2A, IL17F, CD86, PYY, FIGF, NKX3-2, WNT3A, and PDK4, which are genes used in the present specification, are construed as respectively including naturally occurring wild-type genes of GSC, VAV3, FOXA2, LEF1, COMP, AZU1, GRIN2A, IL17F, CD86, PYY, FIGF, NKX3-2, WNT3A, and PDK4, or functional variants thereof.

The expression level may include an expression level of any gene capable of encoding GSC, VAV3, FOXA2, LEF1, COMP, AZU1, GRIN2A, IL17F, CD86, PYY, FIGF, NKX3-2, WNT3A, or PDK4. The expression level may also refer to an expression level of a material at an mRNA or protein stage. Therefore, the composition may include an agent in terms of measuring amounts of mRNA, protein, or a combination thereof, of GSC, VAV3, FOXA2, LEF1, COMP, AZU1, GRIN2A, IL17F, CD86, PYY, FIGF, NKX3-2, WNT3A, or PDK4. In an example embodiment, the agent may specifically bind to a transcriptome of GSC, VAV3, FOXA2, LEF1, COMP, AZU1, GRIN2A, IL17F, CD86, PYY, FIGF, NKX3-2, WNT3A, or PDK4. In various example embodiments, the agent may include a primer, a probe, or an antisense sequence, or combinations of thereof, which specifically binds to mRNA of GSC, VAV3, FOXA2, LEF1, COMP, AZU1, GRIN2A, IL17F, CD86, PYY, FIGF, NKX3-2, WNT3A, or PDK4, or to a complementary sequence of the mRNA. In various example embodiments, the agent may include a primer, a probe, or an antisense sequence, or a combination thereof, which specifically binds to a gene encoding GSC, VAV3, FOXA2, LEF1, COMP, AZU1, GRIN2A, IL17F, CD86, PYY, FIGF, NKX3-2, WNT3A, or PDK4. In various example embodiments, the agent may be screened according to a method known in the art, such as a method of high throughput screening (HTS), and in addition, may be commercially available.

The primer may serve as an initiation point for polymerization using a polymerase. The primer used herein may also be used in nucleic acid amplification. The term "amplification" as used herein may refer to an increase of copy number of a target sequence or a complementary sequence of the target sequence. The nucleic acid amplification may be performed using any method known in the art. For example, the nucleic acid amplification may be performed using a method employing multiple cycles during the amplification or a method performed at a constant temperature. For example, cycling techniques for the amplification may require a heat cycle. An example of a method requiring a heat cycle includes polymerase chain reaction (PCR), which is known in the art. PCR generally includes: thermally denaturing double-stranded DNA to produce single-stranded DNA; annealing a primer to the single-stranded DNA; and synthesizing a complementary strand from the primer. Isothermal amplification may be performed at a constant temperature or a major aspect of the amplification process occurs at a constant temperature. In contrast to PCR, which allows reaction products to be heated to bind to additional primers to separate double strands, an isothermal method uses a strand displacing polymerase in a dependent manner to separate double strands and re-copy a template. Such an isothermal method is different from a method that relies on primer substitution to initiate reiterative template copying, and is rather distinguished as a method that relies on successive reuse or novel synthesis of single primer molecules. The method that relies on primer substitution may be selected from the group consisting of helicase dependant amplification (HDA), exonuclease dependant amplification, recombinase polymerase amplification (RPA), and loop mediated amplification (LAMP). The method that relies on successive reuse or novel synthesis of single primer molecules may be selected from the groups consisting of strand displacement amplification (SDA), nucleic acid based amplification (NASBA), and transcription-mediated amplification (TMA). Depending on the selected amplification method, one set or two or more sets of primers may be used, wherein the primer may be a primer for PCR.

The measuring of mRNA expression levels may be a process for diagnosing prognosis of ovarian cancer or a risk of recurrence of ovarian cancer by determining the presence of mRNA of GSC, VAV3, FOXA2, LEF1, COMP, AZU1, GRIN2A, IL17F, CD86, PYY, FIGF, NKX3-2, WNT3A, or PDK4 and the degree of expression thereof in a biological sample of an individual, thereby measuring amounts of mRNA. As such, mRNA may be measured through direct isolation or by using a primer or probe relative to the mRNA. Examples of analysis methods for the measuring include reverse transcription polymerase chain reaction (RT-PCR), competitive RT-PCR, real-time RT-PCR, RNase protection assay (RPA), northern blotting, nucleic acid microarray including DNA, and any combination thereof. RT-PCR is a method of analyzing RNA, through PCR, by amplifying cDNA obtained by reverse transcription of mRNA. In RT-PCR, the amplification of cDNA may be performed using a pair of primers that specifically bind to the genes above. Following RT-PCR, a band pattern and a band width of a sample may be identified through electrophoresis to thereby determine the expression of mRNA of the genes above and the degree of expression. Compared with a control group, the prognosis of ovarian cancer or the risk of recurrence of ovarian cancer in an individual may be easily determined. Here, the control group may refer to a normal or negative control group including samples of individuals without ovarian cancer or completely cured individuals. The control group may also refer to a positive control group including samples of individuals currently suffering from ovarian cancer or experiencing recurrence of ovarian cancer.

The term "primer" as used herein may refer to a nucleic acid sequence including a free 3'-terminus hydroxyl group and being capable of forming a base pair with a template complementary to a specific base sequence, and serving as an initiation point for transcription of a template strand. The primer may initiate DNA synthesis in the presence of four different nucleoside triphosphates and a reagent for polymerization in a suitable buffer solution at an appropriate temperature (i.e., DNA polymerase or reverse transcriptase). For example, as a primer specific to mRNA of GSC, VAV3, FOXA2, LEF1, COMP, AZU1, GRIN2A, IL17F, CD86, PYY, FIGF, NKX3-2, WNT3A, or PDK4, a sense and antisense primer set including 7 to 50 nucleotide sequences may be used to perform PCR amplification to measure an amount of a desired product, thereby identifying the prognosis of ovarian cancer or the risk of recurrence of ovarian cancer of an individual. Conditions for PCR and a length of a sense and antisense primer set may be appropriately selected according to techniques known in the art. The primer may include 10 to 100 nucleotides (nts), 15 to 100 nts, 10 to 80 nts, 10 to 50 nts, 10 to 30 nts, 10 to 20 nts, 15 to 80 nts, 15 to 50 nts, 15 to 30 nts, 15 to 20 nts, 20 to 100 nts, 20 to 80 nts, 20 to 50 nts, or 20 to 30 nts.

The term "probe" as used herein may refer to a nucleic acid fragment, such as an RNA or DNA fragment, specifically binding to a target nucleic acid, such as mRNA, and may be labeled so that the presence of specific mRNA and amounts and expression levels of specific mRNA may be determined. The probe may be prepared in the form of an oligonucleotide probe, a single-stranded DNA probe, a double-stranded DNA probe, or an RNA probe. For example, a probe having a nucleic acid sequence complementary to mRNA of GSC, VAV3, FOXA2, LEF1, COMP, AZU1, GRIN2A, IL17F, CD86, PYY, FIGF, NKX3-2, WNT3A, or PDK4 may be used for hybridization, and then, depending on the degree of hybridization, an amount of mRNA may be measured, thereby identifying the prognosis of ovarian cancer or the risk of recurrence of ovarian cancer of an individual. Selection of a suitable probe and conditions for hybridization may be appropriately selected according to techniques known in the art. The probe may include 10 to 100 nts, 15 to 100 nts, 10 to 80 nts, 10 to 50 nts, 10 to 30 nts, 10 to 20 nts, 15 to 80 nts, 15 to 50 nts, 15 to 30 nts, 15 to 20 nts, 20 to 100 nts, 20 to 80 nts, 20 to 50 nts, or 20 to 30 nts.

In addition, the primer or probe may be chemically synthesized according to a solid-phase support synthesis method using phosphoramidite or other synthesis methods widely known in the art. In addition, the nucleic acid sequence may be modified using various methods known in the art. Examples of such modification include methylation, capping, substitution of at least one natural nucleotide with an analog thereof, and modifications between nucleotides, such as modifications with a non-electrically charged linker (e.g., methyl phosphonate, phosphotriester, phosphoramidate, or carbamate) or an electrically charged linker (e.g., phophorotioate or phosphorodithioate). In addition, the primer or probe may be modified using an indicator capable of directly and/or indirectly providing a detectable signal. Examples of the indicator include a radioactive isotope, a fluorescent molecule, and biotin.

The agent may include a peptide or protein that specifically binds to GSC, VAV3, FOXA2, LEF1, COMP, AZU1, GRIN2A, IL17F, CD86, PYY, FIGF, NKX3-2, WNT3A, or PDK4, or mRNA encoding one of these proteins. The peptide or protein may include an antibody, a ligand, a receptor, an agonist, an antagonist, or a fragment thereof, or a combination thereof.

The measuring of protein expression levels may be a process for diagnosing prognosis of ovarian cancer or a risk of recurrence of ovarian cancer by determining the presence of proteins expressed by GSC, VAV3, FOXA2, LEF1, COMP, AZU1, GRIN2A, IL17F, CD86, PYY, FIGF, NKX3-2, WNT3A, or PDK4, and the degree of expression thereof in a biological sample of an individual. As such, an antibody or a fragment thereof capable of directly isolating GSC, VAV3, FOXA2, LEF1, COMP, AZU1, GRIN2A, IL17F, CD86, PYY, FIGF, NKX3-2, WNT3A, or PDK4, or specifically binding to GSC, VAV3, FOXA2, LEF1, COMP, AZU1, GRIN2A, IL17F, CD86, PYY, FIGF, NKX3-2, WNT3A, or PDK4 may be used to identify GSC, VAV3, FOXA2, LEF1, COMP, AZU1, GRIN2A, IL17F, CD86, PYY, FIGF, NKX3-2, WNT3A, or PDK4. The measurement of the protein analysis may be performed by, for example, western blotting, enzyme linked immunosorbent assay (ELISA), radioimmunoassay (RIA), radioimmunodiffusion, Ouchterlony immunodiffusion, rocket immunoelectrophoresis, tissue immunostaining, immunoprecipitation assay, complement fixation assay, fluorescence-activated cell sorting (FACS), mass spectrometry, magnetic bead-antibody immunoprecipitation, a method using a protein chip, or any combination thereof. For example, various types of ELISA include direct ELISA in which a labeled antibody immobilized onto a solid support is used to recognize an antigen, indirect ELISA in which a labeled antibody is used to recognize a capture antibody immobilized on a solid support and bound to an antigen, direct sandwich ELISA in which a secondary antibody is used to recognize an antibody which captures an antigen complexed with a different antibody immobilized onto a solid support, or indirect sandwich ELISA in which a secondary antibody is used to recognize an antibody after the antibody reacts binds to an antigen complexed with a different antibody immobilized onto a solid support. In addition, the expression levels of the proteins may be detected using sandwich ELISA, which enzymatically develops proteins through attachment of a labeled antibody that recognizes an antigen complexed with a different antibody after immobilizing an antibody on a solid support and allowing a reaction on a sample, or enzymatically develops proteins through attachment of a labeled secondary antibody with respect to an antibody that recognizes an antigen complexed with a different antibody. In this regard, the degree of formation of the protein-antibody complex may be determined, thereby identifying the prognosis of ovarian cancer or the risk of recurrence of ovarian cancer of an individual.

For example, the measurement of the protein expression level may be, for example, performed by western blotting using at least one antibody with respect to the protein. Here, all the proteins are separated from a sample, are subjected to electrophoresis to separate them by size, and are migrated to a nitrocellulose membrane where they react with an antibody to form an antigen-antibody complex. Afterwards, the amount of the proteins is identified in the same manner as in identifying an amount of the antigen-antibody complex by using a labeled antibody, and thus the prognosis of ovarian cancer or the risk of recurrence of ovarian cancer of an individual may be identified.

The method of detecting the protein may include comparing the measured protein expression level in the biological sample with that of a normal control group including samples from individuals without ovarian cancer or completely cured individuals without any manipulation. Here, the mRNA or protein expression level may be measured according to an absolute value of the marker (e.g., µg/Ml) or a relative value (e.g., relative extent of signals).

The term "antibody" as a term known in the art may refer to a specialized immunoglobulin which is directed toward an antigenic site. The antibody may specifically bind to GSC, VAV3, FOXA2, LEF1, COMP, AZU1, GRIN2A, IL17F, CD86, PYY, FIGF, NKX3-2, WNT3A, PDK4, or a fragment thereof. Here, a fragment of any of GSC, VAV3, FOXA2, LEF1, COMP, AZU1, GRIN2A, IL17F, CD86, PYY, FIGF, NKX3-2, WNT3A, and PDK4 may be, for example, an immunogenic fragment. Such a fragment may refer to a protein fragment having at least one epitope corresponding to an antibody for GSC, VAV3, FOXA2, LEF1, COMP, AZU1, GRIN2A, IL17F, CD86, PYY, FIGF, NKX3-2, WNT3A, or PDK4. In order to prepare an antibody, GSC, VAV3, FOXA2, LEF1, COMP, AZU1, GRIN2A, IL17F, CD86, PYY, FIGF, NKX3-2, WNT3A, or PDK4 may be cloned into an expression vector, GSC, VAV3, FOXA2, LEF1, COMP, AZU1, GRIN2A, IL17F, CD86, PYY, FIGF, NKX3-2, WNT3A, or PDK4 encoded by the cloned gene may be obtained, and a common method known in the art may be performed on the obtained protein.

The antibody may be in the form of a polyclonal antibody, a monoclonal antibody, or a recombinant antibody, and in this regard, all the immunoglobulin antibodies fall within the range of the antibody of the present inventive concept. The antibody may be in a complete form composed of two full-length light chains and two full-length heavy chains. In addition, the antibody may be a special antibody, such as a humanized antibody. The polyclonal antibody may be prepared according to a conventional method known in the art by injecting an immunogen (e.g., a biomarker protein or a fragment thereof) into a foreign host. The foreign host may include a mammal, such as a mouse, a rat, a sheep, and a rabbit. When the immunogen is injected in an intramuscular, intraperitoneal, or subcutaneous manner, it can be administered with an adjuvant to generally increase antigenicity. Then, blood may be regularly collected from the foreign host to collect serum showing improved titer and specificity for an antigen, or to separate and purify antibodies therefrom.

The monoclonal antibody may be prepared by cell line generation techniques by fusion known to those of skill in the art. For a brief description of a method of preparing the monoclonal antibody, Balb/C mice may be immunized with a suitable amount (e.g., 10 µg) of the protein that has been purified, or polypeptide fragments of the protein may be synthesized and combined with bovine serum albumin to immunize mice, and then, antigen-producing lymphocytes isolated from the mice may be fused with human or mouse myeloma to produce immortalized hybridoma cells. Then, according to ELISA, only hybridoma cells producing desired monoclonal antibodies are selected and cultured, and monoclonal antibodies may be separated and purified from the culture. In addition, the monoclonal antibody may be a commercially available antibody for GSC, VAV3, FOXA2, LEF1, COMP, AZU1, GRIN2A, IL17F, CD86, PYY, FIGF, NKX3-2, WNT3A, or PDK4.

Such antibodies may be used to identify the protein expression in the biological sample according to suitable methods known in the art, such as ELISA, RIA, sandwich assay, or western blotting or immunoblotting on a polyacrylamide gel.

The term "fragment" as used herein may refer to, for example, a polypeptide not having a complete structure of an antibody, peptide, or protein, but having a binding domain or an antigen-binding site that is specifically directed toward an antigenic site. The fragment may include a functional fragment of an antibody molecule that is not an antibody in a complete form consisting of two light chains and two heavy chains. Such a fragment of an antibody molecule may refer to a fragment having at least an antigen-binding function, and may include Fab, F(ab'), F(ab')$_2$, or Fv. The binding fragment may include at least 7 amino acids, and for example, at least 9 amino acids or at least 12 amino acids.

The expression level may refer to an expression level in a sample separated from an individual, and the sample may be separated from ovaries of the individual. Examples of the sample separated from the individual include blood, plasma, serum, urine, feces, saliva, tears, cerebrospinal fluid, cells, tissues, and any combination thereof. The individual may include a mammal, such as a human, a primate, a dog, a cat, a cow, a horse, a pig, a rabbit, or a mouse.

According to one or more embodiments, a kit for diagnosing prognosis of ovarian cancer or a risk of recurrence of ovarian cancer in an individual includes an agent for measuring an expression level of at least one gene selected from the group consisting of GSC, VAV3, FOXA2, LEF1, COMP, AZU1, GRIN2A, IL17F, CD86, PYY, FIGF, NKX3-2, WNT3A, and PDK4

The kit may include, for example, a microarray that measures an expression level of GSC, VAV3, FOXA2, LEF1, COMP, AZU1, GRIN2A, IL17F, CD86, PYY, FIGF, NKX3-2, or PDK4, or an expression level of mRNA of a gene encoding these proteins. The microarray may be prepared according to a known method in the art using GSC, VAV3, FOXA2, LEF1, COMP, AZU1, GRIN2A, IL17F, CD86, PYY, FIGF, NKX3-2, WNT3A, or PDK4. In the microarray, mRNA of a gene encoding GSC, VAV3, FOXA2, LEF1, COMP, AZU1, GRIN2A, IL17F, CD86, PYY, FIGF, NKX3-2, WNT3A, or PDK4, or a cDNA having a sequence corresponding to a fragment of the gene may be attached as a probe on a substrate.

When the kit is used for, for example, measuring an expression level of mRNA of GSC, VAV3, FOXA2, LEF1, COMP, AZU1, GRIN2A, IL17F, CD86, PYY, FIGF, NKX3-2, WNT3A, or PDK4, the kit may include necessary elements to perform RT-PCR. Such an RT-PCR kit may include, in addition to primers each specifically bind to mRNA of marker genes, a test tube or other proper containers; a reaction buffer solution; deoxynucleotides (dNTPs); enzymes, such as a Taq-polymerase and a reverse transcriptase; DNase; an RNase inhibitor; dEPC-water; or sterilized water. In addition, the kit may include a pair of primers each specifically binding to a gene used in a qualitative control group.

In addition, the kit may include a substrate, an appropriate buffer, a secondary antibody labeled with a chromogenic enzyme or a fluorescent substance, or a chromogenic substrate, for detecting an antibody specifically binding to GSC, VAV3, FOXA2, LEF1, COMP, AZU1, GRIN2A, IL17F, CD86, PYY, FIGF, NKX3-2, WNT3A, or PDK4, or for immunological detection of antibodies. The substrate may be a nitrocellulose membrane, a 96-well plate synthesized by a polyvinyl resin, a 96-well plate synthesized by a polystyrene resin, or a glass slide. The chromogenic enzyme may be peroxidase or alkaline phosphatase. The fluorescent substance may be FITC or RITC. The chromogenic substrate may be 2,2'-azino-bis(3-ethylbenzothiazoline-6-sulfonic acid) (ABTS), o-phenylenediamine (OPD), or tetramethyl benzidine (TMB).

According to one or more embodiments, a method of diagnosing prognosis of ovarian cancer or a risk of recurrence of ovarian cancer of an individual for providing necessary information related to diagnosing prognosis of ovarian cancer or a risk of recurrence of ovarian cancer of an individual includes: forming a complex by contacting a sample separated from an individual with one or more materials specifically binding to one or more proteins selected from GSC, VAV3, FOXA2, LEF1, COMP, AZU1, GRIN2A, IL17F, CD86, PYY, FIGF, NKX3-2, WNT3A, and PDK4, or one or more mRNAs encoding any of these proteins; measuring an expression level of one or more genes selected from GSC, VAV3, FOXA2, LEF1, COMP, AZU1, GRIN2A, IL17F, CD86, PYY, FIGF, NKX3-2, WNT3A, and PDK4 in the sample by measuring a level of the complex; comparing the measured expression level of the selected one or more genes in the sample with that of the same gene(s) in a control group; and, in the case of changes in the expression level of the one or more genes in the sample as compared with the control group, determining whether the individual has poor prognosis of ovarian cancer or a high risk of recurrence of ovarian cancer.

The method may include forming a complex by contacting a sample separated from an individual with the materials each specifically binding to GSC, VAV3, FOXA2, LEF1, COMP, AZU1, GRIN2A, IL17F, CD86, PYY, FIGF, NKX3-2, WNT3A, PDK4, or an mRNA encoding any of these proteins.

The expression level may include a protein expression level of GSC, VAV3, FOXA2, LEF1, COMP, AZU1, GRIN2A, IL17F, CD86, PYY, FIGF, NKX3-2, WNT3A, or PDK4. Thus, the measuring of the expression level may be performed by measuring an amount of mRNA of GSC, VAV3, FOXA2, LEF1, COMP, AZU1, GRIN2A, IL17F, CD86, PYY, FIGF, NKX3-2, WNT3A, or PDK4, proteins, or a combination thereof.

The method may also include measuring an expression level of GSC, VAV3, FOXA2, LEF1, COMP, AZU1, GRIN2A, IL17F, CD86, PYY, FIGF, NKX3-2, WNT3A, or PDK4 in a sample by measuring a level of the complex.

The measuring of the level of the complex may be performed by detecting signals from a detectable label attached to a material that specifically binds to any of the proteins above or an mRNA encoding any of the proteins above. The measuring of the level of the complex may be a step of measuring a level of any of the proteins above or an mRNA encoding any of the proteins above after separating the complex again; a step of measuring a level of the material that specifically binds to any of the proteins above or an mRNA encoding any of the proteins above; or a step of measuring a level of the complex without separating the complex. The measuring of the level of the complex may be performed by RT-PCR, competitive RT-PCR, real-time RT-PCR, RPA, northern blotting, nucleic acid microarray including DNA, western blotting, ELISA, RIA, radioimmunodiffusion, Ouchterlony immunodiffusion, rocket immunoelectrophoresis, tissue immunostaining, immunoprecipitation assay, complement fixation assay, FACS, mass spectrometry, magnetic bead-antibody immunoprecipitation, protein chip, or a combination thereof.

The method may include comparing the measured expression level of the one or more genes selected from GSC, VAV3, FOXA2, LEF1, COMP, AZU1, GRIN2A, IL17F, CD86, PYY, FIGF, NKX3-2, WNT3A, or PDK4 in the sample with that of the same gene(s) in a control group.

The method may also include determining that the individual has poor prognosis of ovarian cancer or a high risk of recurrence of ovarian cancer in the case of higher expression levels of the selected gene(s) in the sample than in the normal or negative control group. In addition, the method may also include determining that the individual does not have poor prognosis of ovarian cancer or has a low risk of recurrence of ovarian cancer in the case of lower expression levels of the selected gene(s) in the sample than in the control or negative group.

The method may also include determining, if the expression level of GSC, VAV3, FOXA2, LEF1, COMP, AZU1, GRIN2A, IL17F, CD86, PYY, FIGF, NKX3-2, WNT3A, or PDK4 in the individual is changed relative to that of the same gene(s) in a control group, whether the individual has poor prognosis of ovarian cancer or has a high risk of recurrence of ovarian cancer. Such a change in the expression level in the individual may refer to an expression level similar with that in a normal or negative control group; or an expression level increased by at least 1%, 2%, 3%, 4%, 5%, 10%, 20%, 30%, 40%, 50%, 60%, 70%, 80%, 90%, 100%, 200%, 300%, 400%, 500%, 600%, 700%, 800%, 900%, or 1,000% as compared with that in a normal or negative control group. In addition, such a change in the expression level in the individual may refer to an expression level similar with that in a positive control group; or an expression level decreased by at least 1%, 2%, 3%, 4%, 5%, 10%, 20%, 30%, 40%, 50%, 60%, 70%, 80%, 90%, or 100% as compared with that in a positive control group.

The method may include evaluating clinicopathologic parameters of a patient, such as chemoresistance, lymph node metastasis, and distant metastasis of cancer cells, or patient survival.

According to one or more embodiments, a composition for treating ovarian cancer or preventing recurrence of ovarian cancer includes an agent to inhibit an expression level of VAV3.

The agent may be effective in inhibition of spheroid-forming capacity of cancer cells, inhibition of colony formation of cancer cells, inhibition of proliferation or growth of cancer cells, or enhancement of sensitivity to other anticancer treatments, thereby directly and/or indirectly treating ovarian cancer or predicting recurrence of ovarian cancer. Here, the cancer cells may be CSCs.

The agent may specifically bind to VAV3 or an mRNA sequence encoding the protein. The agent may inhibit expression of VAV3 by binding to VAV3 or the mRNA sequence encoding the protein.

The agent may be a nucleotide binding to a sequence of VAV3 in a complementary manner. The nucleotide may have a length of 5, 6, 7, 8, 9, 10, 11, 12, 13, 14, 15, 16, 17, 18, 19, 20, 25, 30, 35, 40, 50, 60, 70, 80, 90, or 100 nts. The nucleotide may include a sequence having homology of at least 100%, 99%, 98%, 97%, 96%, 95%, 90%, 85%, 80%, 75%, or 70% with the sequence of VAV3, but may also include all sequences that can bind to the sequence of VAV3 in a complementary manner. For example, the nucleotide may be an siRNA, and the nucleotide may have a sequence of SEQ ID NO: 1 or 2.

The agent may be an antibody or a fragment thereof, which specifically binds to VAV3.

The composition may further include a pharmaceutically acceptable carrier. The term "pharmaceutically acceptable carrier" as used herein denotes a material that is used in combination with an active ingredient, that is, generally, an inert material, to help application of the active ingredient. Examples of the pharmaceutically acceptable carrier may include, in general, a pharmaceutically acceptable excipient, additive, or diluent. Examples of the pharmaceutically acceptable carrier may include at least one selected from the group consisting of a filler, a binder, a disintegrant, a buffer, a preservative, an antioxidant, a lubricant, a flavoring agent, a thickener, a coloring agent, an emulsifier, a suspending agent, a stabilizer, and an isotonic agent.

The composition may include the agent for reducing expression level of VAV3 at a "therapeutically effective amount". In the composition, the term "therapeutically effective amount" as used herein refers to a sufficient amount that produces a therapeutic effect when administered to a subject in need of treatment. The term "treatment" as used herein refers to treatment of a disease or medical condition, for example, ovarian cancer, including humans, and the meaning of treatment is: (a) preventing the occurrence of the disease or medical condition, that is, by prophylactic treatment of a patient; (b) ameliorating the disease or medical condition such as by eliminating or causing regression of the disease or medical condition of a patient; (c) suppressing the disease or medical condition such as by slowing or arresting the development of the disease or medical condition of a patient; or (d) alleviating a symptom of the disease or medical condition of a patient. The composition may include an "effective amount of an agent for reducing expression of VAV3 in a cancer cell of a mammal". The "effective amount" may be appropriately selected by one of ordinary skill in the art. For example, the "effective amount" may be in a range of about 0.01 mg to about 10,000 mg, 0.1 mg to about 1000 mg, about 1 mg to about 100 mg, about 0.01 mg to about 1000 mg, about 0.01 mg to about 100 mg, about 0.01 mg to about 10 mg, or about 0.01 mg to about 1 mg. The composition may include an agent for reducing expression of VAV3 as an active ingredient. The term "active ingredient" refers to an ingredient enabling a function of the composition as described above, but excludes the case where the amount of the active ingredient is so small to act like impurities.

The composition may be prepared for oral administration or parenteral administration including intravenous, intraperitoneal, subcutaneous, rectal, and topical administration. Thus, the composition may be formulated into various forms such as tablets, capsules, aqueous solutions, or suspensions. In the case of tablets for oral administration, an excipient such as lactose or corn starch and a lubricant such as magnesium stearate may be added thereto in general. In the case of capsules for oral administration, lactose and/or dried corn starch may be used as a diluent. When an aqueous suspending agent for oral administration is needed, active ingredients may be attached to an emulsifier and/or a suspending agent. If necessary, a predetermined sweetening agent and/or a flavoring agent may be added to the composition. For intraneural, intramuscular, intraperitoneal, subcutaneous, and intravenous administration, a sterilized solution of the active ingredients is generally prepared, wherein the pH of the sterilized solution needs to be appropriately adjusted and buffered. For intravenous administration, the total concentration of solutes needs to be controlled to render the formulated composition isotonic. The composition may be formulated into an aqueous solution including a pharmaceutically acceptable carrier such as salt water at a pH of 7.4. The aqueous solution may be administered to intramuscular or intraneural blood flow of a patient by local bolus injection.

According to one or more embodiments, a method of treating ovarian cancer or preventing recurrence of ovarian cancer includes administering a composition to an individual, the composition including an agent to lower an expression level of the VAV3 gene.

The method of treating ovarian cancer or preventing recurrence of ovarian cancer may include:

forming a complex by contacting a sample separated from an individual with a material that specifically binds to at least one protein selected from GSC, VAV3, FOXA2, LEF1, COMP, AZU1, GRIN2A, IL17F, CD86, PYY, FIGF, NKX3-2, WNT3A, and PDK4, and an mRNA encoding any of these proteins; measuring expression levels of at least one gene selected from GSC, VAV3, FOXA2, LEF1, COMP, AZU1, GRIN2A, IL17F, CD86, PYY, FIGF, NKX3-2, WNT3A and PDK4 in the sample by measuring levels of the complex; comparing the measured expression levels of the selected gene(s) in the sample with those of the same gene(s) in a control group; and determining that the individual has poor prognosis of ovarian cancer or a high risk of recurrence of ovarian cancer in the case of changes in the expression level of the one or more genes in the sample as compared with the control group. In this regard, depending on detection levels of disease markers in the individual, pharmaceutically active substances may be administered to the individual, thereby providing personalized diagnosis and treatment.

According to one or more embodiments, a method of treating ovarian cancer or preventing recurrence of ovarian cancer includes: administering a candidate material to an individual; separating a sample from the individual, the sample including a target cell; forming a composition by contacting the separated sample with a material that specifically binds to VAV3 or an mRNA encoding the protein; measuring an expression level of VAV3 in the sample by measuring a level of the composition; comparing the measured expression level of the gene in the sample with those of the same gene in a control group; and determining, if the expression level of the gene in the sample is changed relative to that of the same gene in a control group, the candidate material to have an influence in treating ovarian cancer or preventing recurrence of ovarian cancer.

The method may include administering of the candidate material to the individual. The candidate material may be a material expected to have an influence in treating ovarian cancer or preventing recurrence of ovarian cancer. A method of administering the candidate material may be appropriately selected according to a material to be used. For example, the route of administration may be any means, such as intravenous, intramuscular, oral, transdermal, mucosal, intranasal, intratracheal, or subcutaneous administration. The material to be used in the method may be administered systemically or locally, and for example, may be administered to the ovary.

The method may also include determining of, if the expression level of VAV3 in the individual is changed relative to that of the same gene in a control group, the candidate material to have an influence in treating ovarian cancer or preventing recurrence of ovarian cancer. The changes in the expression levels in the individual may refer to expression levels increased by at least 1%, 2%, 3%, 4%, 5%, 10%, 20%, 30%, 40%, 50%, 60%, 70%, 80%, 90%, 100%, 200%, 300%, 400%, 500%, 600%, 700%, 800%, 900%, and 1000% as compared with those in a control group; or expression levels decreased by at least 1%, 2%, 3%, 4%, 5%, 10%, 20%, 30%, 40%, 50%, 60%, 70%, 80%, 90%, 100% as compared with those in a control group.

Hereinafter, the present inventive concept will be described in detail by explaining preferred embodiments of the inventive concept. However, the preferred embodiments should be considered in descriptive sense only and not for purposes of limitation.

Example 1: Selection of Markers of Poor Prognosis of Ovarian Cancer

1. Materials and Experiment Methods (1) Patients and Tissue Samples

For isolation and evaluation of CSCs, tumor cells of high-grade OSCs were obtained, primarily at the time of surgery, from 17 patients who had undergone oophorectomy for ovarian carcinoma, and then cultured. A spheroid formation assay was performed using the cultured primary cancer cells.

36 fresh tissue samples of high-grade OSCs were obtained from the patients, and then, used for qRT-PCR analysis to validate mRNA expression for differentially expressed genes in the cDNA microarray. The clinicopathological characteristics of the patients are shown in Table 1.

Here, fallopian tubes of patients undergoing hysterectomy with salpingectomy due to benign myoma uteri were used as healthy controls.

For immunohistochemical (IHC) analysis, formalin-fixed paraffin-embedded tissues obtained from 74 high-grade OSC patients being treated at the Bundang CHA Medical Center were used. The clinicopathological characteristics of the patients are shown in Table 1.

Here, histologic diagnosis and clinical stages adhere to the World Health Organization (WHO) classification. Histologic stages followed a two-tiered grading system, and tumor stages followed the tumor-node-metastasis staging (TNM) system.

The samples were divided into a chemosensitive group and a chemoresistant group according to responsiveness to first-line chemotherapy (taxol/platinum-based combination therapy) after surgery.

The present study was approved by the Ethics Committee of the Bundang CHA Medical Center, and was carried out with informed consent obtained from all patients.

TABLE 1

Clinicopathological characteristics of patients subjected to quantitative real-time PCR analysis and immunohistochemical staining

|  | Total | Chemosensitive | Chemoresistant |
|---|---|---|---|
| qRT-PCR analysis |  |  |  |
| Age (years) | 57.4 ± 11.3 | 56.6 ± 11.3 | 58.8 ± 11.7 |
| Stage |  |  |  |
| I/II (%) | 5 (13.9) | 5 (21.7) | 0 (0) |
| III/IV (%) | 31 (86.1) | 18 (78.3) | 13 (100) |

TABLE 1-continued

Clinicopathological characteristics of patients subjected to quantitative real-time PCR analysis and immunohistochemical staining

|  | Total | Chemosensitive | Chemoresistant |
|---|---|---|---|
| Nodal metastasis | | | |
| Absent (%) | 17 (47.2) | 11 (47.8) | 6 (46.2) |
| Present (%) | 19 (52.8) | 12 (52.2) | 7 (53.8) |
| Distant metastasis | | | |
| Absent (%) | 26 (72.2) | 16 (69.6) | 10 (76.9) |
| Present (%) | 10 (27.8) | 7 (30.4) | 3 (23.1) |
| Total (%) | 36 | 23 (68.9) | 13 (36.1) |
| IHC analysis | | | |
| Age (years) | 53.8 ± 10.4 | 52.0 ± 9.8 | 59.2 ± 10.4 |
| Stage | | | |
| I/II (%) | 14 (18.9) | 14 (25.5) | 0 (0) |
| III/IV (%) | 60 (81.1) | 41 (74.5) | 19 (100) |
| Nodal metastasis | | | |
| Absent (%) | 35 (47.3) | 28 (50.9) | 7 (36.8) |
| Present (%) | 39 (52.7) | 27 (49.1) | 12 (63.2) |
| Distant metastasis | | | |
| Absent (%) | 38 (51.4) | 30 (54.5) | 8 (42.1) |
| Present (%) | 36 (48.6) | 25 (45.5) | 11 (57.9) |
| Recurrence | | | |
| Absent (%) | 34 (45.9) | 29 (52.7) | 5 (26.3) |
| Present (%) | 40 (54.1) | 26 (47.3) | 14 (73.7) |
| Total (%) | 74 | 55 (74.3) | 19 (25.7) |

IHC: Immunohistochemistry;
qRT-PCR: quantitative real-time polymerase chain reaction (2) Primary Cell Culture and Spheroid-Forming Cell Isolation Primary tumor cells were obtained at the time of surgery from 17 high-grade OSC patients who had undergone oophorectomy. A tumor mass was cut into small pieces and enzymatically digested into single-cell suspensions and incubated in $Ca^{2+}/Mg^{2+}$-free phosphate-buffered saline containing 50 U/mL of collagenase A (Roche, Pleasanton, Calif.). Cells were incubated with Ber-EP4-coated magnetic Dynabeads (Life Technologies, Grand Island, N.Y.) to select epithelial cells, and then, cultured in RPMI medium (Gibcoo/Life Technologies, Grand Island, N.Y.) containing 10% fetal bovine serum, 1% penicillin-streptomycin, and 20 ng/mL epidermal growth factor (Life Technologies).

For the spheroid formation assay, single cells were plated on an ultralow-attachment 6-well culture plate (Corning, Acton, Mass.) at a density of $1 \times 10^3$ cells/$cm^2$ in a serum-free Dulbecco's modified Eagles's medium (Life Technologies) supplemented with 20 ng/mL epidermal growth factor (Life Technologies), 10 ng/mL basic fibroblast growth factor (Sigma-Aldrich, St Louis, Mo.), 0.4% bovine serum albumin (Sigma-Aldrich), and 5 μg/mL insulin (Sigma-Aldrich). Spheroid formation of 50-100 cells was assessed at 7 days after seeding. The spheroid-forming efficiency was defined as the ratio of colonies/cells seeded per well.

(3) cDNA Microarray Analysis

The cDNA microarray was performed on four spheroid-forming cell (SFC) samples and corresponding primary cancer cells.

CSCs were obtained using the iScript cDNA synthesis kit (Bio-Rad, Reymond, Wash.), and synthesis of target cDNA probes and hybridization were performed using the Agilent's Low RNA Input Linear Amplification kit (Agilent Technology, Santa Clara, Calif.). Amplified and labeled cRNAs were purified on the cRNA Cleanup Module (Agilent Technology). The fragmented cRNAs were directly pipetted onto assembled Human Oligo Microarrays (60K) (Aligent Technology).

The hybridized images were scanned using a DNA microarray scanner, and then, quantified with Feature Extraction Software (Agilent Technology). Data normalization and selection of significantly changed genes were performed using GeneSpring GX 7.3 (Agilent Technology). The averages of normalized ratios were calculated by dividing the average normalized signal channel intensity by the average normalized control channel intensity. Functional annotation of genes was performed according to the Gene Ontology Consortium (www.geneontology.org/index.shtml) by GeneSpring GX 7.3. Gene classification was performed based on DAVID (http://david.abcc.ncifcrf.gov/) and Medline database (www.ncbi.nlm.nih.gov/).

(4) Qualitative Real-Time PCR

Total RNA was isolated from tissues or primary cells using TRIzol reagent (Life Technologies). Synthesis of first-strand cDNA was performed using the Superscript III kit (Life Technologies). Real-time PCR was performed in triplicate using the CFX96 real-time PCR detection system (Bio-Rad Laboratories, Hercules, Calif.). 20 μL of the final reaction product included 0.5 μL of cDNA template, 10 μL of TaqMAn Master Mix (Applied Biosystems, Paisley, United Kindom), and 1 μL of a mixture of primers and probes. Transcript levels were normalized versus glyceraldehyde-3-phosphate dehydrogenase (GAPDH) expression. The gene expression was calculated using the formula $2^{-\Delta\Delta Ct}$.

(5) Tissue Microarray and IHC Staining

For the IHC analysis, 74 OSC samples were used to construct a tissue microarray. For each sample, two tissue cores with diameters of 3 mm were punched out from each tissue mass, and then, arranged into paraffin blocks using a manual microarray device (UNITMA; Quick-RAY™ UNITech Science, Seoul, Korea). Tissue microarray paraffin sections were deparaffinized in xylene. Endogenous peroxidase activity was blocked with 0.3% hydrogen peroxide. For antigen retrieval, the sections were heated in 0.1 M citrate buffer (pH 6.0) for 15 minutes in a microwave oven.

Slides were incubated overnight at a temperature of 4□ with the following primary antibodies and working dilutions: FOXA2 (1:200; Abcam, Cambridge, United Kingdom), LEF1 (1:250; Abcam), PYY (1:50; Abcam), VAV3 (1:50; Novus Biologicals, Littleton, Colo.), NKX3-2 (1:75; Novus Biologicals), and Wnt3A (1:750; Novus Biologicals). The slides were then incubated with a secondary antibody for 15-30 minutes using the HRP Polymer Ultravision LP Detection System (Thermo Scientific, Waltham, Mass.) at room temperature. The sections were then developed with diaminobenzidine and counterstained with hematoxylin. The IHC stains were interpreted by two independent pathologists.

Protein expression was determined by an immunoreactive score. The percentage of positive cells was scored as 0 (negative), 1 (<10% positive cells), 2 (<10-50% positive cells), 3 (<51-75% positive cells), or 4 (>75% positive cells). The staining intensity was categorized as 0 (negative), 1 (weak), 2 (moderate), or 3 (strong). The final immunoreactive score was calculated by multiplying these two scores.

(6) Functional Assay for VAV3

Transfection of VAV3 siRNA

For the functional assay for VAV3, paclitaxel (PTX)-resistant SKpac cells, which were generated by continuous exposure of SKOV3 (ATCC, Manassas, Va.) cells to a stepwise escalating concentration of PTX over 8 months, were used. VAV3 siRNA and negative siRNA (as a normal control group) were synthesized by Invitrogen (Carlsbad, Calif.). The day before transfection, 1×10⁵ cells were seeded into each well of a six-well plate. The next day, the cells were transfected with annealed siRNA oligos using Lipofectamine 2000 (Invitrogen) according to the manufacturer's instructions. At 24 hours and 48 hours after transfection, the cells were harvested, and the efficiency of VAV3 knockdown after siRNA transfection was confirmed by qRT-PCR. The cells were then prepared for MTT, colony formation, and spheroid formation assays.

(7) MTT Analysis for Cell Viability

Cells (1×10⁴) were seeded into a 96-well culture plate, and subsequently treated with 10 pmol VAV3 siRNA in a culture medium for 24 hours and 48 hours. Control cells were treated with 10 pmol negative siRNA in a culture medium. After 24 hours and 48 hours, the cells were incubated with MTT reagent (0.5 mg/mL) at a temperature of 37□ for 4 hours. The resulting formazan crystals were solubilized by the addition of 100 µL DMSO to each well.

(8) Colony Formation Assay

Cells were seeded into each well of a 6-well plate at a density of 1×10⁵ cells per well. The next day, the cells were transfected with siRNA, and then, incubated for 48 hours. Transfected cells were then replated in a gelatin-coated 6-well culture dish at a density of 300 cells per well. After 14 days, colonies were visualized using hematoxylin after fixation with 4% paraformaldehyde for 10 minutes. Groups including more than 50 cells were scored as colonies.

(9) Statistical Analysis

Statistical analysis was conducted using the SPSS statistics software package (IBM SPSS Statistics Data Editor 20). The relations between mRNA and protein expression levels in each tumor group and clinicopathologic factors were evaluated by $\chi^2$ analysis, Fisher's exact test, or the Mann-Whitney test. For survival analysis, the Kaplan-Meier method and the Cox proportional hazards model were used. The results of each functional assay are expressed as mean±standard error. The Student's t-test was performed and P<0.05 was considered significant.

2. Screening of SFC-Specific Biomarkers to Assess Pathologic Status of Ovarian Cancer (1) Confirmation of Presence of Large Amounts of CSCs within SFCs Isolated from Cultured Primary Cells from Human Ovarian Carcinomas (OCSs)

Figure 1B:
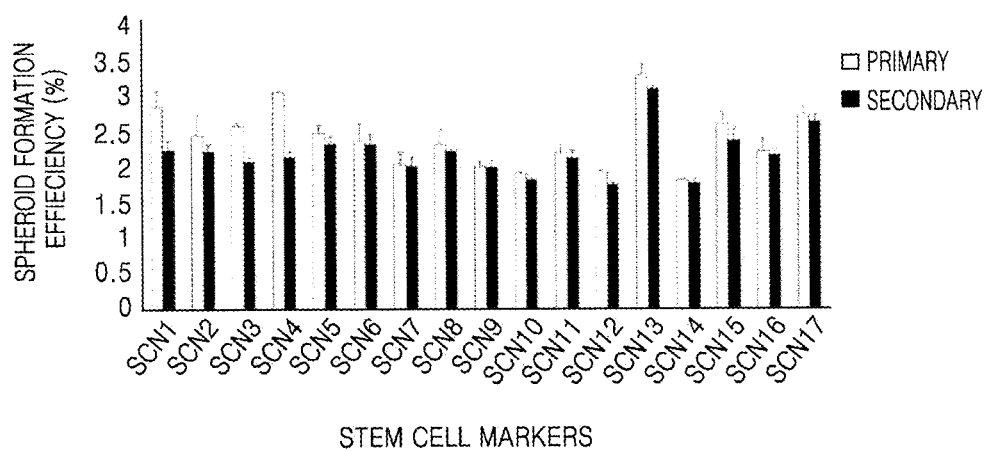

The non-adherent spherical clusters of 50-100 cells were observed 1 week after plating for the spheroid formation assay (see FIG. 1A). The SFCs were collected, and then, the spheroid-forming capacity thereof was assessed. The efficiency of spheroid formation from the inoculated cells was about 2.37%±0.4% in the first generation. These floating spheres were enzymatically dissociated, and single cells were harvested and used to form secondary spheroids under the same culture conditions. The spheroid-forming capacity in the second generation was similar to the first generation (2.17%±0.3%) (see FIG. 1B and Table 2).

TABLE 2

Primary and secondary spheroid-forming capability of OCSs

| | Primary (%) | Secondary (%) |
|---|---|---|
| SCN1 | 2.82 | 2.21 |
| SCN2 | 2.42 | 2.2 |

TABLE 2-continued

Primary and secondary spheroid-forming capability of OCSs

| | Primary (%) | Secondary (%) |
|---|---|---|
| SCN3 | 2.55 | 2.05 |
| SCN4 | 3.01 | 2.12 |
| SCN5 | 2.45 | 2.31 |
| SCN6 | 2.33 | 2.3 |
| SCN7 | 2.01 | 1.98 |
| SCN8 | 2.3 | 2.19 |
| SCN9 | 1.98 | 1.97 |
| SCN10 | 1.88 | 1.8 |
| SCN11 | 2.17 | 2.1 |
| SCN12 | 1.89 | 1.73 |
| SCN13 | 3.25 | 3.06 |
| SCN14 | 1.79 | 1.75 |
| SCN15 | 2.57 | 2.34 |
| SCN16 | 2.19 | 2.14 |
| SCN17 | 2.7 | 2.61 |
| Mean ± SD | 2.37 ± 0.4 | 2.17 ± 0.3 |

SCN: serous carcinoma;
SD: standard deviation

Figure 1C:
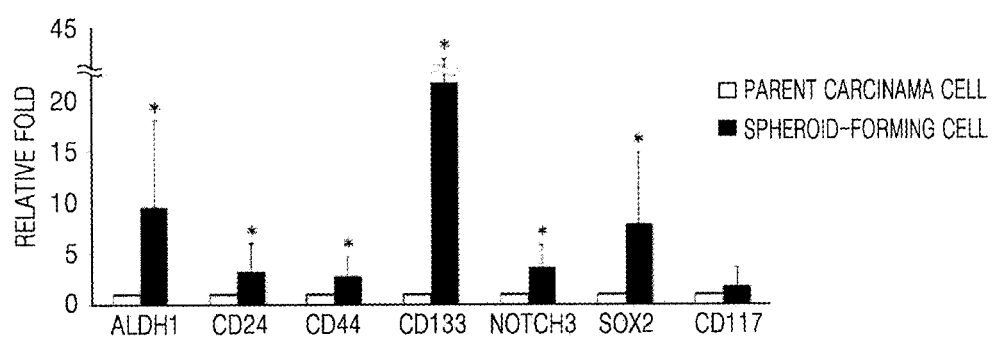

To examine whether the CSCs were enriched in SFCs, the mRNA expression of the well-known stem cell marker was analyzed in the SFCs by qRT-PCR, and the analysis results are compared with those of the parental primary cancer cells. The stem cell markers being assessed herein are ALDH1, CD24, CD44, CD133, NOTCH3, SOX2, and CD117. All of these stem cell markers, except CD117, were more highly expressed in the SFCs than in the primary cancer cells (P<0.05). Thus, it was confirmed that the CSCs were enriched in the SFCs (see FIG. 1C), and such SFCs were referred as CSC-like cells.

Figure 2A:
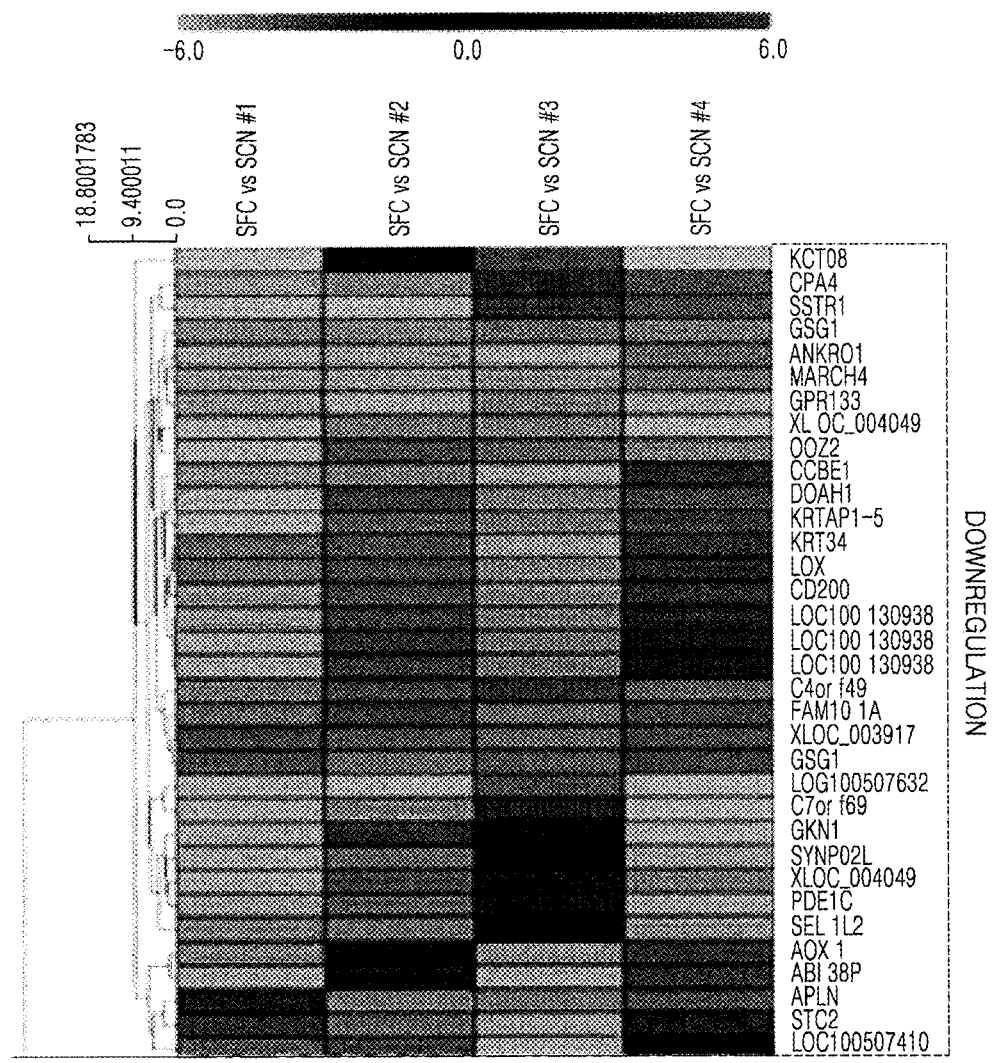
FIGS. 2A to 2C shows results of cDNA microarray analysis of OSC SFCs and the corresponding primary cancer cells.
Figure 2A:

(2) Confirmation of Gene Expression Profiles of CSC-Like Cells by cDNA Microarray The cDNA microarray was performed to assess the gene expression profile of the spheroid-forming CSC-like cells. Gene expression was compared between four samples of CSC-like cells and their corresponding parental primary cancer cells. Consequently, it was confirmed that the expression of 619 genes was significantly increased or decreased at least 5-fold in the CSC-like cells as compared with the control cancer cells (P<0.05). Among these genes, 381 exhibited increased expression, and 238 exhibited decreased expression. In particular, hierarchical clustering of 62 genes that were significantly altered more than 15-fold in the CSC-like cells is shown in FIG. 2A. The microarray data presented herein were prepared according to the Minimum Information About a Microarray Experiment (MIAME) recommendations, and are accessible through the Gene Expression Omnibus (GEO) Series accession number GSE60765 (www.ncbi.nlm.nih.gov/geo).

Figure 2B:
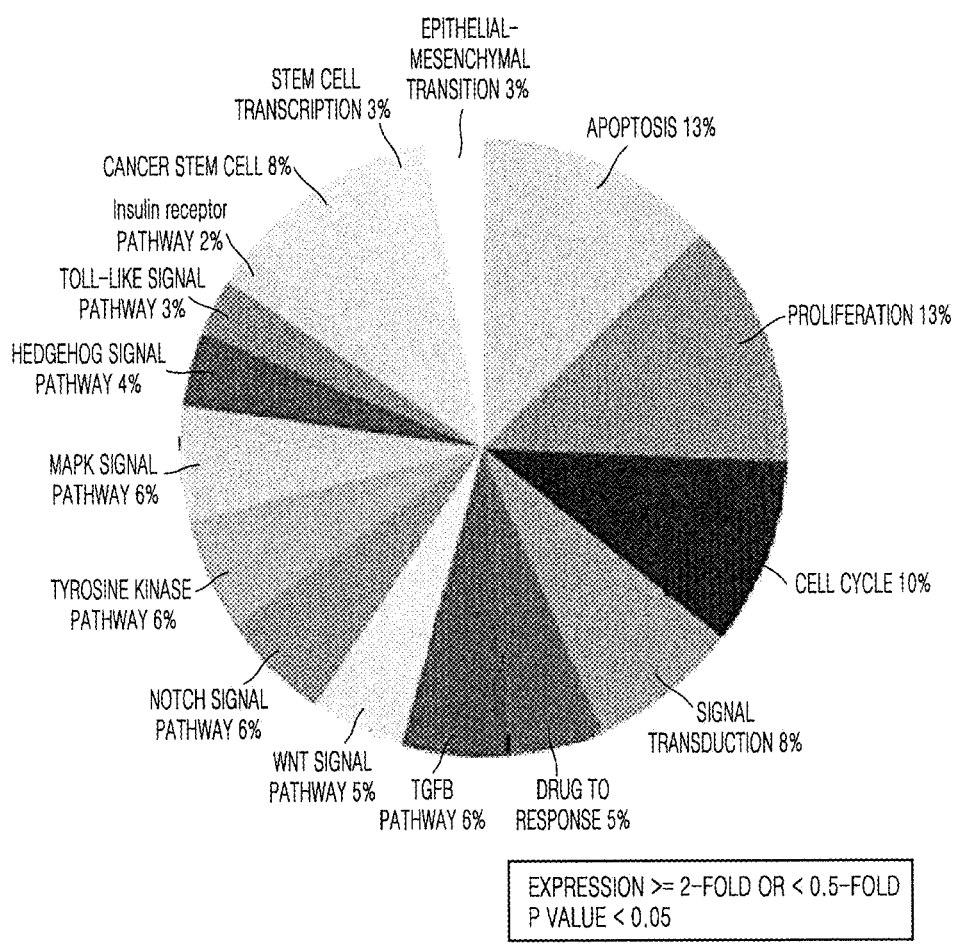

The genes that were increased or decreased in their expression by at least 2-fold in the CSC-like cells were classified according to biological process gene ontology. FIG. 2B provides a pie chart showing the proportion of genes representing each process. Referring to FIG. 2B, the genes present in the greatest number were associated with apoptosis and proliferation (13% each); followed by cell cycle (10%); CSC (8%) and signal transduction (8%); transforming growth factor-β (TGF-β) (6%); mitogen-activated protein kinase (MAPK) (6%); tyrosine kinase (6%) and Notch signaling (6%); drug response (5%); and Wnt signal transduction (5%); hedgehog signaling (4%); epithelial-mesenchymal transition (3%) and Toll-like signaling (3%); and insulin receptor pathway (2%).

Among the CSC markers, CD24 (13.85-fold), ALDH1A1 (6.80-fold), and SOX2 (5.36-fold) were significantly upregulated in spheroid-forming CSC-like cells. The onco-genesis-related genes, which were increased more than 5-fold in CSC-like cells as compared with the control cancer cells, and their associated functions are summarized in Table 3.

based on the results of the cDNA microarray and gene ontology. In particular, genes upregulated more than 5-fold in CSC-like cells by cDNA microarray were identified, and then, the most highly expressed genes associated with onco-genesis were selected therefrom. The relative expression

TABLE 3

Genes known to be related with oncogenesis and upregulated more than 5-fold in CSCs as compared with primary cancer cells

| Genes | | Function | Relative fold | P-value |
|---|---|---|---|---|
| AGT | Angiotensinogen (serpin peptidase inhibitor, clade A, member 8) | SIG | 7.13 | <0.05 |
| ALDH1A1 | Aldehyde dehydrogenase 1 family, member A1 | CSC | 6.8 | <0.05 |
| ANK3 | Ankyrin 3, node of Ranvier (ankyrin G) | SIG | 8.27 | <0.05 |
| AZU1 | Azurocidin 1 | APO | 13.36 | <0.05 |
| CD24 | CD24 molecule | CSC | 13.85 | <0.05 |
| CD86 | CD86 molecule | PRO | 8.67 | <0.05 |
| COL15A1 | Collagen, type XV, alpha 1 | SIG | 8.95 | <0.05 |
| COMP | Cartilage oligomeric matrix protein | APO | 15.34 | <0.05 |
| DNAH17 | Dynein, axonemal, heavy chain 17 | SIG | 5.64 | <0.05 |
| EGR3 | Early growth response 3 | SCT | 5.36 | <0.05 |
| FIGF | c-fos-induced growth factor (vascular endothelial growth factor D) | PRO, SIG, NOT | 14.01 | <0.05 |
| FOXA2 | Forkhead box A2 | SIG, SCT | 15.11 | <0.05 |
| GRIN2A | Glutamate receptor, ionotropic, N-methyl-D-aspartate 2A | SIG, DRU | 7.34 | <0.05 |
| GSC | Goosecoid homeobox | EMT | 8.39 | <0.05 |
| HEYL | Hairy/enhancer of split related with YRPW motif-like | EMT, NOT | 5.36 | <0.05 |
| HGF | Hepatocyte growth factor (hepapoietin A; scatter factor) | EMT, APO, PRO, CYC, SIG | 6.66 | <0.05 |
| IL17F | Interleukin 17F | SIG | 17.36 | <0.05 |
| LEF1 | Lymphoid enhancer-binding factor 1 | EMT, APO, SIG, WNT | 28.76 | <0.05 |
| MMP10 | Matrix metallopeptidase 10 (stromelysin 2) | SIG | 25.87 | <0.05 |
| NKX3-2 | NK3 homeobox 2 | APO | 9.43 | <0.05 |
| NR6A1 | Nuclear receptor subfamily 6, group A, member 1 | PRO | 5.15 | <0.05 |
| NTRK2 | Neurotrophic tyrosine kinase, receptor, type 2 | TYR | 5.76 | <0.05 |
| NUMB | Numb homolog (Drosophila) | NOT | 9.13 | <0.05 |
| OR10A7 | Olfactory receptor, family 10, subfamily A, member 7 | SIG | 20.94 | <0.05 |
| OR1N2 | Olfactory receptor, family 1, subfamily N, member 2 | SIG | 5.15 | <0.05 |
| OR2T4 | Olfactory receptor, family 2, subfamily T, member 4 | SIG | 7.02 | <0.05 |
| OR9G4 | Olfactory receptor, family 9, subfamily G, member 4 | SIG | 5.37 | <0.05 |
| PDGFRB | Platelet-derived growth factor receptor, beta polypeptide | TYR | 5.4 | <0.05 |
| PDK4 | Pyruvate dehydrogenase kinase, isozyme 4 | INS, TYR | 11.83 | <0.05 |
| POU4F1 | POU class 4 homeobox 1 | SCT | 6.84 | <0.05 |
| PROC | Protein C (inactivator of coagulation factors, Va and VIIIa) | APO | 6.74 | <0.05 |
| PYY | Peptide YY | PRO | 11.98 | <0.05 |
| RASD1 | RAS, dexamethasone-induced 1 | SIG | 5.79 | <0.05 |
| SERPINF1 | Serpin peptidase inhibitor, clade F, member 1 | PRO | 6.41 | <0.05 |
| SOX2 | SRY (sex-determining region Y)-box 2 | CSC, SCT | 5.36 | <0.05 |
| SPEN | Spen homolog, transcriptional regulator (Drosophila) | NOT, TYR, WNT | 5.64 | <0.05 |
| SYCE1 | Synaptonemal complex central element protein 1 | CYC | 8 | <0.05 |
| TNFSF10 | Tumor necrosis factor (ligand) superfamily, member 10 | SIG, NOT, TGF | 6.72 | <0.05 |
| TRIL | TLR4 interactor with leucine-rich repeats | TOL | 7.19 | <0.05 |
| UCN2 | Urocortin 2 | PRO | 6.95 | <0.05 |
| VAV3 | vav 3 guanine nucleotide exchange factor | SIG | 11.75 | <0.05 |
| WN73A | Wingless-type MMTV integration site family, member 3A | PRO, WNT, HED | 6.19 | <0.05 |

APO: apoptosis;
CSC: cancer stem cell marker;
CYC: cell cycle;
DRU: drug response;
EMT: epithelial mesenchymal transformation;
HED: hedgehog pathway;
INS: insulin receptor;
NOT: Notch signaling pathway;
PRO: proliferation;
SCT: stem cell transcription;
SIG: signal transduction;
TGF: transforming growth factor-β pathway;
TOL: Toll-like receptor signaling pathway;
TYR: tyrosine kinase signaling;
WNT: Wnt pathway.

(3) Selection of 14 Genes as Candidates for Biomarkers and Validation by qRT-PCR To identify candidate biomarkers for predicting poor prognosis and chemoresistance, 14 genes were selected levels of these 14 genes were as follows: GSC (8.39-fold), VAV3 (11.75-fold), FOXA2 (15.11-fold), LEF1 (28.76-fold), COMP (15.34-fold), AZU1 (13.36-fold), GRIN2A (7.34-fold), IL17F (17.36-fold), CD86 (8.67-fold), PYY (11.98-fold), FIGF (14.01-fold), NKX3-2 (9.43-fold), WNT3A (6.19-fold), and PDK4 (11.83-fold).

Figure 2C:
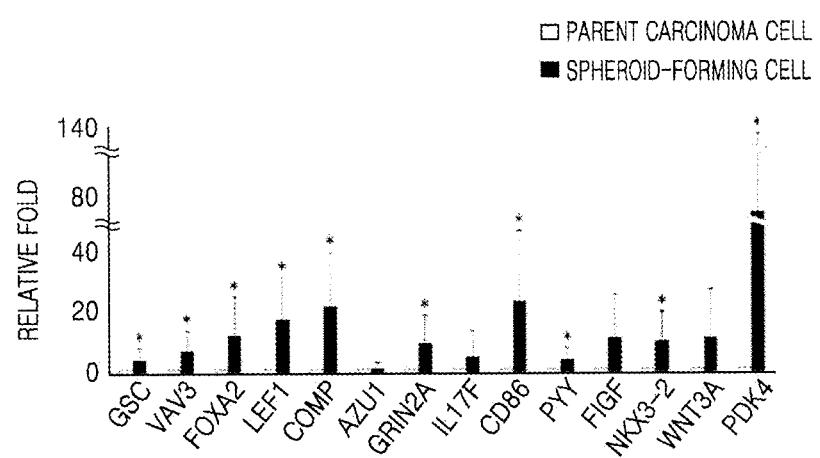

In addition, the mRNA expression levels of these 14 genes in the SFCs and their parental cancer cells were validated by qRT-PCR. Consequently, it was confirmed that GSC (4.26-fold; P<0.001), VAV3 (7.05-fold; P<0.001), FOXA2 (12.06-fold; P<0.05), LEF1 (17.26-fold; P<0.05), COMP (21.33-fold; P<0.001), GRIN2A (9.36-fold; P<0.001), CD86 (23.14-fold; P<0.001), PYY (4.18-fold; P<0.001), NKX3-2 (10.35-fold; P<0.001), and PDK4 (74.26-fold; P<0.001) were significantly upregulated in SFCs as compared with parental cancer cells (see FIG. 2C).

(4) Validation of Increased Expression Levels of LEF1, PYY, NKX3-2, and WNT3A in Chemoresistant Cancer Cells To assess the mRNA expression of the candidate genes, qRT-PCR was performed on 36 fresh human OSC tissues. Then, the mRNA expression levels in the OSC tissues were compared with those in normal fallopian tubes (controls).

Consequently, it was confirmed that the following 11 genes were significantly overexpressed in the human OSCs: VAV3 (7.92-fold), FOXA2 (7.32-fold), LEF1 (9.64-fold), COMP (25.01-fold), GRIN2A (12.51-fold), IL17F (2.50-fold), CD86 (6.35-fold), PYY (13.50-fold), NKX3-2 (10.79-fold), WNT3A (15.67-fold), and PDK4 (10.19-fold) (all P<0.05).

Figure 3A:
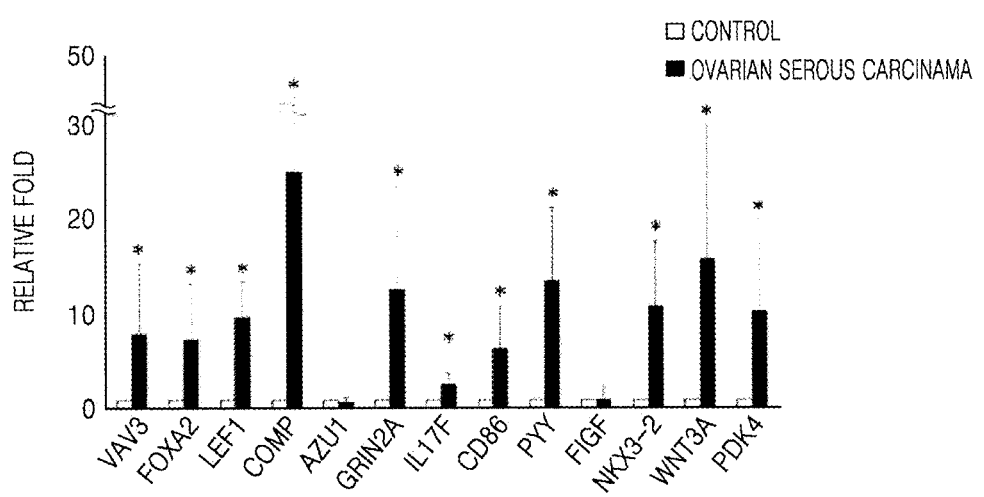
FIG. 3A is a graph showing mRNA expression levels of genes selected by qRT-PCR, wherein the mRNA expression levels of 13 genes are significantly increased in SFCs as compared with those of primary cancer cells, and 11 genes are significantly overexpressed in OSCs as compared with control fallopian tubes (*P<0.05)
Figure 3B:
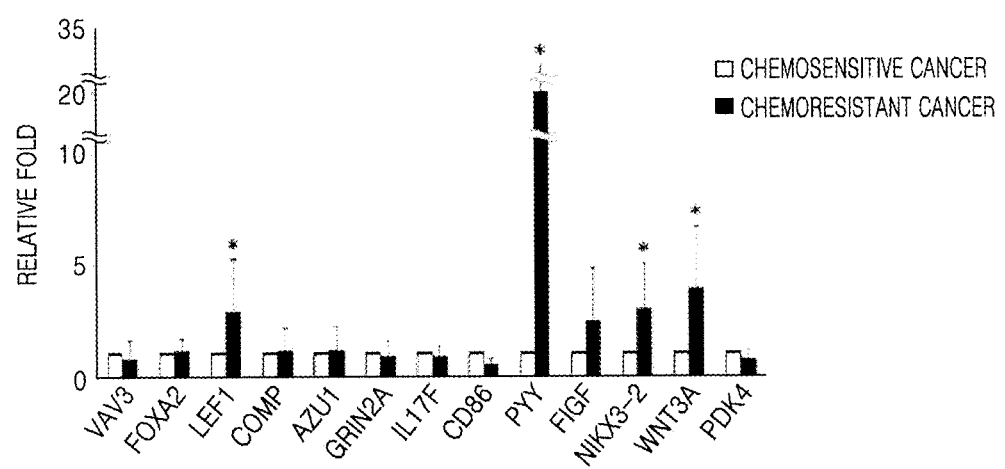
FIG. 3B is a graph indicating that the relative mRNA levels of LEF1, PYY, NKX3-2, and WNT3A genes are significantly increased in chemoresistant cancer cells as compared with those in chemosensitive cancer cells.

FIG. 3A shows the relative expression of 13 candidate genes in the OSCs and controls. Referring to FIG. 3A, LEF1, PYY, NKX3-2, and WNT3A showed significant differences in their expression levels between OSCs and controls (P<0.05). In particular, the expression level of LEF1 was increased about 2.85-fold, the expression level of PYY was increased about 20.03-fold, the expression level of NKX3-2 was increased about 3.02-fold, and the expression level of WNT3A was increased about 3.91-fold in the OSCs, which are chemoresistant cancer cells, as compared with chemosensitive cells (controls) (see FIG. 3B).

Figure 3C:
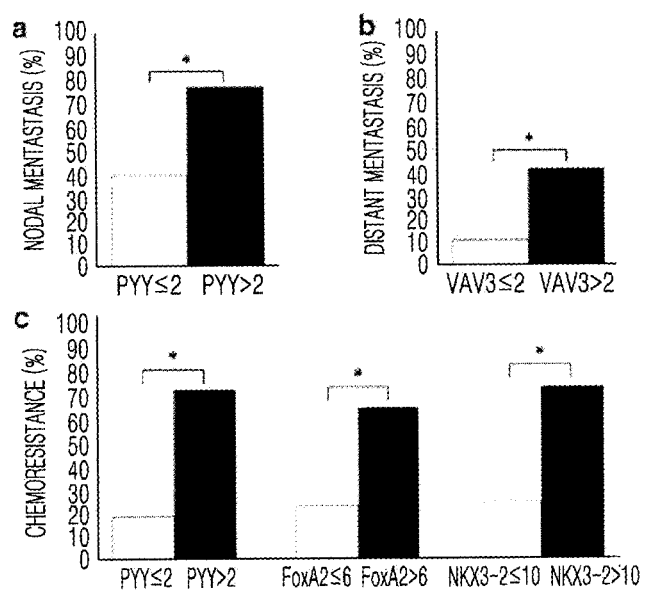
FIG. 3C is a graph showing associations between clinicopathologic parameters and the mRNA expression levels identified by qRT-PCR, wherein (a) shows significant association between the expression level of PYY (≥2-fold increase) and lymph node metastasis (*P<0.05), (b) shows significant association between the expression level of VAV3 (≥2-fold increase) and distant metastasis (*P<0.05), and (c) shows association between the expression levels of PYY (≥2-fold increase), FOXA2 (≥6-fold increase), and NKX3-2 (≥10-fold increase) and increased chemoresistance in OSCs (*P<0.05)

Furthermore, the correlation between the mRNA expression levels and clinicopathologic parameters was analyzed, and it was confirmed that the increased expression of VAV3 (>2-fold relative to normal controls) was associated with distant metastasis (P<0.05). Likewise, the increased expression of PYY (>2-fold relative to normal controls) was associated with lymph node metastasis (P<0.05) and chemoresistance (P<0.05), and the increased expression of FoxA2 (>6-fold relative to normal controls) and NKX3-2 (>10-fold relative to normal controls) were associated with chemoresistance (P<0.05) (see FIG. 3C).

(5) Validation of Correlation Between Overexpression of VAV3, NKX3-2, and LEF1 in OSCs and Poor Prognosis An IHC study was performed on a tissue microarray including 74 OSC tissue samples to validate the protein expression of the candidate genes and to assess the association between the protein expression of these genes and clinicopathologic parameters, such as clinical state, lymph node, distant metastasis, chemoresistance, and survival. As targets for the study, six proteins, i.e., LEF1, PYY, NKX3-2, WNT3A6, VAV3, and FOXA2, were selected. When the immunoreactive score was ≥4 for LEF1, NKX3-2, PYY, and Wnt3A; ≥2 for FOXA2; and ≥6 for VAV3, the samples were considered as exhibiting overexpression.

Figure 4A:
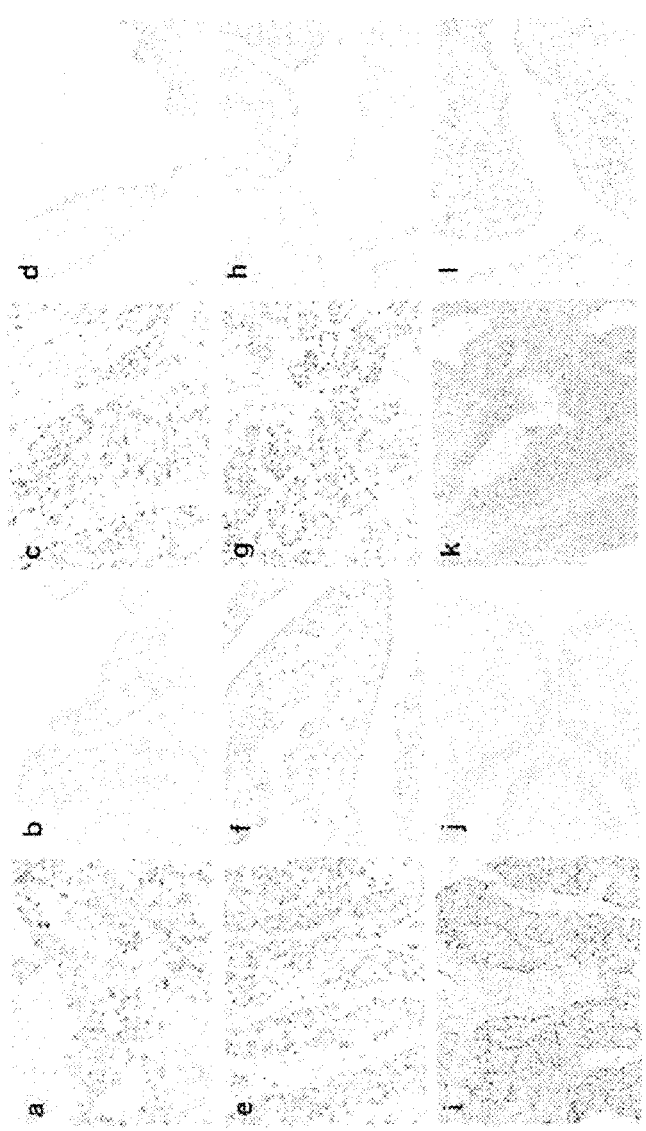
FIG. 4A are images showing immunohistochemical staining of OSCs and control tissues, wherein (a,b) indicate positive nuclear staining for FOXA2 in OCSs but negative staining in fallopian tubes, (c,d) indicate positive nuclear staining for LEF1 in OSCs, but negative staining in fallopian tubes, (e,f) indicate positive nuclear and cytoplasmic reactivity for VAV3 in OCSs, but negative staining in fallopian tubes, (g,h) indicate NKX3-2 staining in the nuclei of OSCs, but no staining in fallopian tubes, (i,j) indicate membranous staining for Wnt3A in OSCs, but only luminal staining in fallopian tubes, and (k,l) indicate PYY-positive staining in OSCs, but negative staining in fallopian tubes.
Figure 4B:
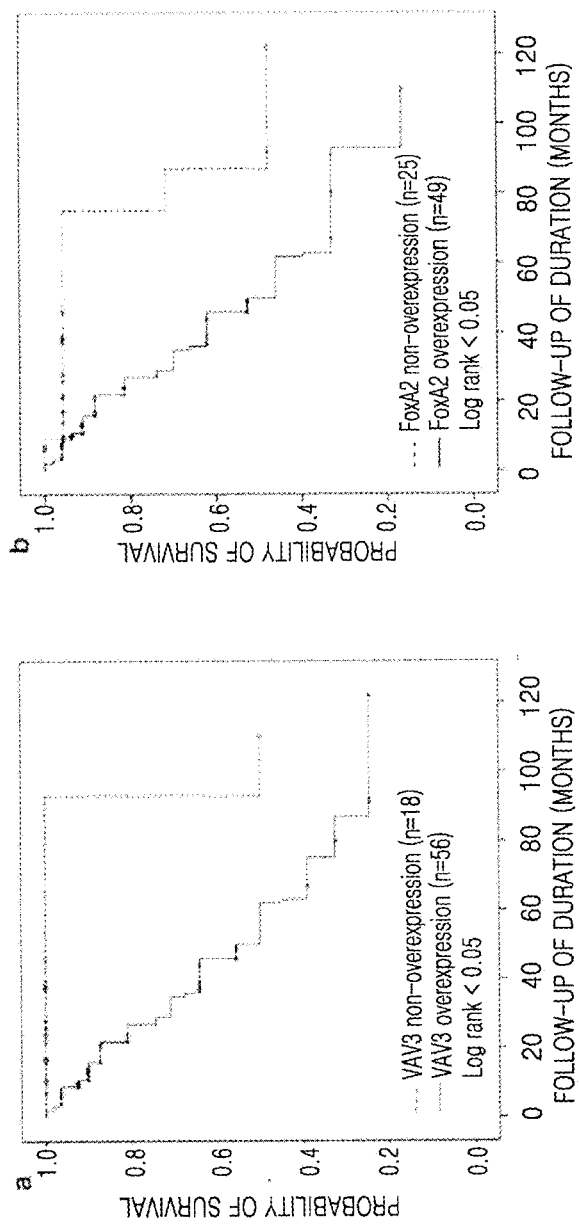
FIG. 4B shows survival curves according to VAV3 and FOXA2 immunohistochemical reactivity, indicating that patients with high levels of VAV3 (a) or FOXA2 (b) expression show poorer survival than patients with low VAV3 or FOXA2 expression ($P<0.05$)

Consequently, staining was observed in the cytoplasm or the nucleus of the OSC tissue, focally or diffusely (see FIG. 4A). In particular, FOXA2, LEF1, and NKX3-2 showed nuclear positivity, PYY showed cytoplasmic positivity, and VAV3 showed both nuclear and cytoplasmic positivity.

The epithelial and stromal cells of benign serous cystadenomas and normal fallopian tubes were negative or weakly positive (less than 5% positive cells) for FOXA2, LEF1, NKX3-2, and VAV3.

Apical staining for Wnt3A was found in epithelial cells of normal fallopian tubes and benign serous cystadenomas, whereas membranous staining was observed in OSC tissues.

The majority of OSCs overexpressed these proteins. In particular, FOXA2 was overexpressed in 66.2% (49/74) of cases; LEF1 was overexpressed in 59.5% (44/74) of cases; and PYY, NKX3-2, and Wnt3A were overexpressed in 58.1% (43/74), 58.1% (43/74), and 63.5% (47/74) of cases, respectively. The relationships between IHC staining and clinicopathologic parameters are shown in Table 4. Referring to Table 4, distant metastasis was significantly related to the expression of LEF1, VAV3, and NKX3-2 (P<0.05), and chemoresistance was significantly related to the overexpression of NKX3-2 (P<0.05).

TABLE 4

Relationships between immunohistochemical expression and clinicopathologic parameters in OSCs (N = 74)

| | FOXA2 | | LEF1 | | VAV3 | | PYY | | NKX3-2 | | Wnt3A | |
|---|---|---|---|---|---|---|---|---|---|---|---|---|
| | OE | P-value | OE | P-value | OE | P-value | OE | P-value | OE | P-value | OE | P-value |
| Age | | | | | | | | | | | | |
| <55 | 24/42 | 0.059 | 24/42 | 0.642 | 31/42 | 0.668 | 25/42 | 0.777 | 22/42 | 0.253 | 28/42 | 0.519 |
| ≥55 | 25/32 | | 20/32 | | 25/32 | | 18/32 | | 21/32 | | 19/32 | |
| Clinical stage | | | | | | | | | | | | |
| I and II | 9/14 | 0.865 | 7/14 | 0.423 | 9/14 | 0.270 | 7/14 | 0.495 | 5/14 | 0.059 | 10/14 | 0.494 |
| III and IV | 40/60 | | 37/60 | | 47/60 | | 36/60 | | 38/60 | | 37/60 | |
| Nodal metastasis | | | | | | | | | | | | |
| Absent | 23/35 | 0.931 | 19/35 | 0.390 | 10/35 | 0.420 | 22/35 | 0.433 | 19/35 | 0.528 | 20/35 | 0.281 |
| Present | 26/39 | | 25/39 | | 31/39 | | 21/39 | | 24/39 | | 27/39 | |
| Distant metastasis | | | | | | | | | | | | |
| Absent | 24/38 | 0.568 | 18/38 | <0.05[a] | 23/38 | <0.05[a] | 24/38 | 0.366 | 17/38 | <0.05[a] | 23/38 | 0.583 |
| Present | 25/36 | | 26/36 | | 33/36 | | 19/36 | | 26/36 | | 24/36 | |
| Chemoresistance | | | | | | | | | | | | |
| Sensitive | 35/55 | 0.425 | 31/55 | 0.356 | 42/55 | 0.814 | 33/55 | 0.575 | 28/55 | <0.05[a] | 35/55 | 0.970 |
| Resistance | 14/19 | | 13/19 | | 14/19 | | 10/19 | | 15/19 | | 12/19 | |

[a]p < 0.05. A sample was considered OE (overexpression) when the immunoreactive score was ≥2 for FOXA2, ≥4 for LEF1, PYY, NKX3-2, and Wnt3; and ≥6 for VAV3.

Example 2. Validation of Effects of VAV3 Knockdown Using VAV3 siRNA in CSCs

(1) Validation of Associations Between High VAV3 Immunoreactivity and Poor Prognosis in OSCs A survival analysis was performed for 74 OSC patients according to their protein expression. Experiment materials and methods used herein were the same as those described in connection with Example 1. The protein expression was analyzed by immunohistochemistry. The median follow-up period was 31 months (1-112 months). During the follow-up period, 21 patients (28.4%) died of disease. According to the Kaplan-Meier analysis, it was found that the overexpression of VAV3 (immunoreactive score 6) and FOXA2 (immunoreactive score 2) was significantly associated with short overall survival (OS) (VAV3, OS: 64.2% in overexpressed cells vs. 94.4% in controls, P<0.05; FOXA2, OS: 63.3% in overexpressed cells vs. 88% in controls, P<0.05). The expression of other proteins was not associated with patient survival.

A multivariate Cox regression analysis was performed for clinicopathological parameters and the immunoreactivity of VAV3 and FOXA2. The overexpression of VAV3 was found to be an independent indicator of poor prognosis in OSC patients (see Table 5; hazard ratio: 15.27, P<0.05). However, the overexpression of FOXA2 was not significantly associated with OS in the present analysis. In addition, chemoresistance was significantly associated with poor survival (hazard ratio: 17.74, P<0.001)

TABLE 5

Multivariate Cox regression analysis for clinicopathologic parameters and immunohistochemical expression of VAV3 and FOXA2

|  | No. of cases (n = 74) | Death | Overall survival | Hazard ratio | P-value |
|---|---|---|---|---|---|
| Age |  |  |  |  |  |
| <55 | 42 | 9 | 35.0 ± 29.7 | 2.38 | 0.134 |
| ≥55 | 32 | 12 | 26.5 ± 23.1 |  |  |
| Clinical stage |  |  |  |  |  |
| I/II | 14 | 1 | 38.8 ± 24.2 | 3.83 | 0.220 |
| III/IV | 60 | 20 | 29.6 ± 27.7 |  |  |
| Distant metastasis |  |  |  |  |  |
| Absent | 38 | 10 | 38.6 ± 27.1 | 1.10 | 0.877 |
| Present | 36 | 11 | 23.6 ± 25.4 |  |  |
| Chemoresistance |  |  |  |  |  |
| Sensitive | 55 | 13 | 37.0 ± 29.1 | 17.74 | <0.05$^a$ |
| Resistant | 19 | 8 | 15.0 ± 9.1 |  |  |
| VAV3 expression |  |  |  |  |  |
| Low | 18 | 1 | 33.1 ± 27.5 | 15.27 | <0.05$^a$ |
| High | 56 | 20 | 30.8 ± 27.3 |  |  |
| FOXA2 expression |  |  |  |  |  |
| Low | 25 | 3 | 33.0 ± 30.5 | 2.51 | 0.222 |
| High | 49 | 18 | 30.5 ± 25.6 |  |  |

$^a$P < 0.05.

(2) Effect of Inhibition of VAV3 Knockdown on Spheroid Formation and Validation of Decreased Cancer Cell Viability and Proliferation 1) Spheroid Formation Assay With VAV3 siRNA (SEQ ID NO: 1 or 2) treatment (i.e., addition of VAV3 siRNA to cancer cells), VAV3 knockdown cells were compared with controls with respect to their number and size of spheroids to validate the effect of VAV3 siRNA on CSC activation by VAV3 siRNA.

Figure 5A:
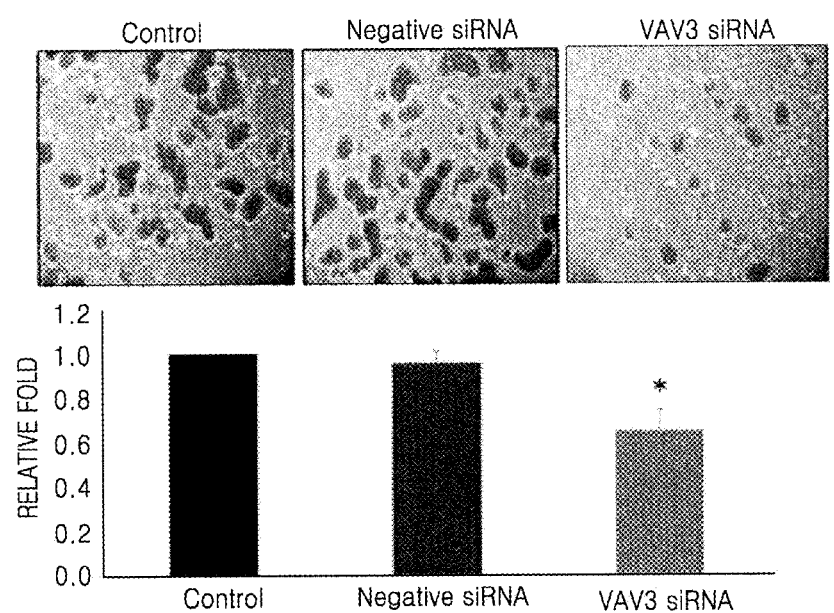
FIGS. 5A to 5C show effects of VAV3 knockdown on paclitaxel (PTX)-resistant ovarian cancer cells.

Consequently, the number of the spheroids formed in CSCs significantly decreased after the treatment with VAV3 siRNA (30% decrease compared with negative siRNA controls, P<0.001), and the size of the spheroids was also significantly decreased (see FIG. 5A). That is, it was confirmed that VAV3 knockdown inhibited CSC activation.

2) Colony Formation Assay

Figure 5B:
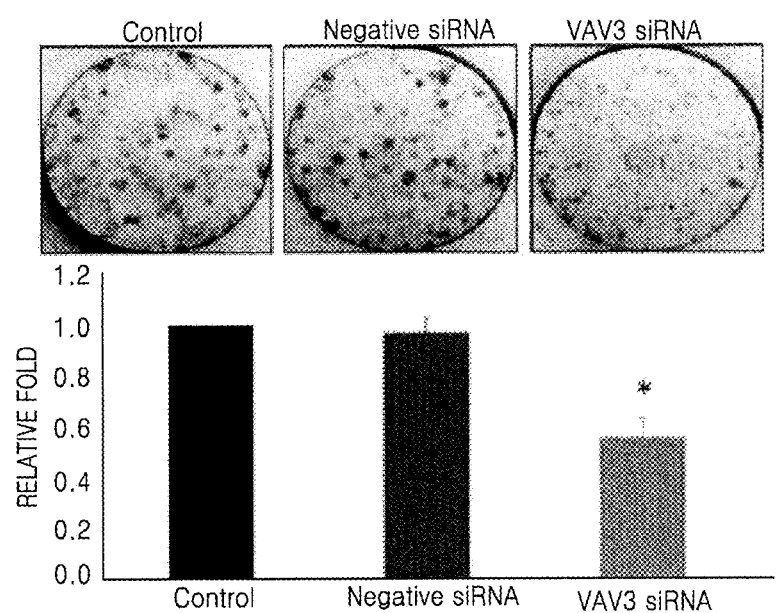

According to the colony formation assay, it was confirmed that clonal growth of SKpac cells was significantly inhibited by VAV3 siRNA. In particularly, the number of colonies of SKpac cells treated with VAV3 siRNA decreased by 41% as compared with the control cells treated with negative siRNA (P<0.001) (see FIG. 5B).

3) PTX Drug Sensitivity Assay

The effects of VAV3 inhibition on sensitivity to PTX of PTX-resistant SKpac cells were assessed. In particular, the cell viability was examined using an MTT assay.

Figure 5C:
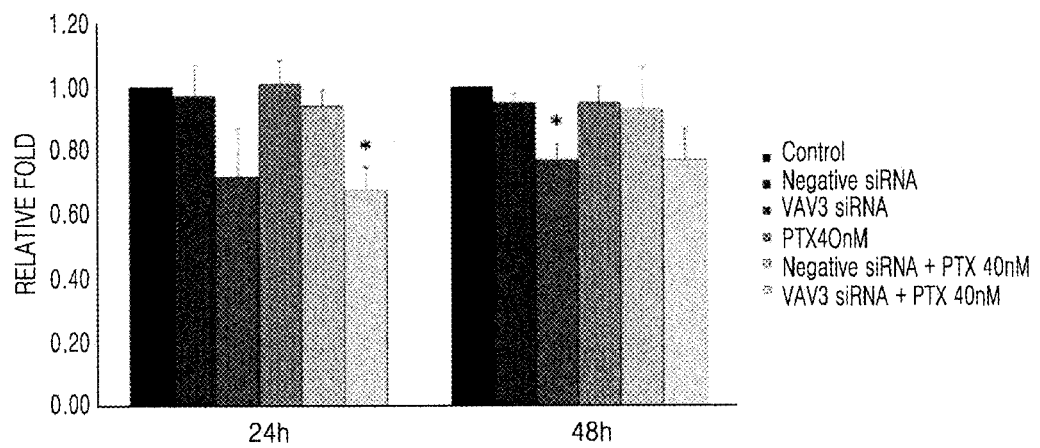

Consequently, it was confirmed that the number of SKpac cells decreased by 27% and 16% at 24 hours and 38 hours, respectively, (P<0.05) upon the addition of VAV3 siRNA+PTX, as compared with the addition of PTX+negative siRNA (controls) (see FIG. 5C).

As described above, according to the one or more of the above example embodiments of the present inventive concept, a composition, a kit, and a method of diagnosing prognosis of ovarian cancer or a risk of recurrence of ovarian cancer of an individual may be used efficiently. According to the one or more of the above example embodiments of the present inventive concept, a composition may be used efficiently to treat ovarian cancer or prevent recurrence of ovarian cancer. According to the one or more of the above example embodiments of the present inventive concept, a method of screening a material for treating ovarian cancer or preventing recurrence of ovarian cancer may be used efficiently to select a candidate material capable of treating ovarian cancer or preventing recurrence of ovarian cancer.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of treating ovarian cancer in a subject in need thereof, the method comprising:
    forming complexes with at least five materials specifically binding with the VAV3, FOXA2, LEF1, NKX3-2, and WNT3A proteins or at least five mRNA encoding these proteins with a sample comprising ovarian cells;
    detecting the complexes;
    measuring an expression level of VAV3, FOXA2, LEF1, NKX3-2, and WNT3A in the ovarian cells in the sample by measuring a level of the complex;
    comparing the measured expression level of the VAV3, FOXA2, LEF1, NKX3-2, and WNT3A in the sample with that of the same genes in a control group; and,
    when the expression level of the genes in the sample as compared with the control group is increased, administering an ovarian cancer therapy to the subject.

2. The method of claim 1, wherein the one or more materials are independently selected from a primer, a probe, a nucleotide, an antibody or an antigen-binding fragment thereof, a ligand, a receptor, an agonist or an antagonist, a protein, or any combination thereof.

3. The method of claim 1, further comprising measuring the expression level of VAV3, FOXA2, LEF1, NKX3-2, and WNT3A proteins or at least five mRNA encoding these proteins.

4. The method of claim 1, wherein the detecting is performed by a reverse transcription polymerase chain reaction (RT-PCR), competitive RT-PCR, real-time RT-PCR, RNase protection assay (RPA), northern blotting, nucleic acid microarray using DNA, western blotting, enzyme-linked immunosorbent assay (ELISA), radioimmunoassay (RIA), radioimmunodiffusion, Ouchterlony immunodiffusion, rocket immunoelectrophoresis, tissue immunostaining, immunoprecipitation assay, complement fixation assay, fluorescence-activated cell sorting (FACS), mass spectrometry, magnetic bead-antibody immunoprecipitation, protein chip, or any combination thereof.

* * * * *